(12) United States Patent
Hillenkamp

(10) Patent No.: US 6,723,564 B2
(45) Date of Patent: *Apr. 20, 2004

(54) IR MALDI MASS SPECTROMETRY OF NUCLEIC ACIDS USING LIQUID MATRICES

(75) Inventor: Franz Hillenkamp, Muenster (DE)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/074,936

(22) Filed: May 7, 1998

(65) Prior Publication Data

US 2001/0055811 A1 Dec. 27, 2001

(51) Int. Cl.[7] .................. G01N 33/48; G01N 33/50; G01N 27/64; H01J 49/00; B01D 59/44
(52) U.S. Cl. ..................... 436/94; 436/43; 436/86; 436/91; 436/93; 436/173; 436/174; 436/181
(58) Field of Search .................. 436/43, 91, 93–94, 436/86, 173, 174, 181

(56) References Cited

U.S. PATENT DOCUMENTS

| | | | |
|---|---|---|---|
| 3,568,735 A | 3/1971 | Lancaster | 141/238 |
| 3,776,700 A | 12/1973 | Gallant | 422/65 |
| 3,807,235 A | 4/1974 | Lefkovitz | 73/863.32 |
| 3,999,689 A | 12/1976 | Ciantro et al. | 222/108 |
| 4,139,346 A | 2/1979 | Rabbani | 422/56 |
| 4,214,159 A | 7/1980 | Hillenkamp et al. | 250/288 |
| 4,442,354 A | 4/1984 | Hurst et al. | 250/281 |
| 4,461,328 A | 7/1984 | Kenney | 422/100 |
| 4,548,245 A | 10/1985 | Crandell et al. | 141/237 |
| 4,554,839 A | 11/1985 | Hewett et al. | 73/864.16 |
| 4,582,789 A | 4/1986 | Sheldon, III et al. | 435/6 |
| 4,683,194 A | 7/1987 | Saiki et al. | 435/6 |
| 4,683,195 A | 7/1987 | Mullis et al. | 435/6 |
| 4,725,677 A | 2/1988 | Köster et al. | 536/27 |
| 4,729,947 A | 3/1988 | Middendorf et al. | 435/6 |
| 4,731,335 A | 3/1988 | Brigati | 436/180 |
| 4,757,141 A | 7/1988 | Fung et al. | 536/27 |
| 4,778,993 A | 10/1988 | Waugh | 250/287 |

(List continued on next page.)

FOREIGN PATENT DOCUMENTS

| | | |
|---|---|---|
| DE | 3221681 | 12/1983 |
| DE | 3930312 | 4/1990 |
| DE | 4011991 | 10/1990 |
| EP | 0268237 | 5/1988 |
| EP | 0269520 | 6/1988 |
| EP | 0339781 | 11/1989 |
| EP | 0360677 | 3/1990 |
| EP | 0396116 | 11/1990 |
| EP | 0412883 | 2/1991 |
| EP | 0455905 | 11/1991 |

(List continued on next page.)

OTHER PUBLICATIONS

K. Harada et al, *Org. Mass Spectrom*, 1982, 17, 386–391.*
W. Aberth et al, *Anal. Chem.* 1982, 54, 2029–2034.*
L. Grotjahn et al, *Int. J. Mass. Spectrom, Ion, Phys.* 1983, 46, 439–442.*
H. Kambara *Springer Ser. Chem. Phys.* 1984, 36, 357–362.*
L. Grotjahn *Springer Proc. Phys.* 1986, 9, 118–125.*
T. Yoshida et al. *Shitsungo Bunseki* 1988, 36, 59–69.*
L. Li et al. *Rev. Sci. Instrum.* 1988, 59, 557–561.*
C. Dass et al. *Anal. Chem.* 1988, 60, 2723–2729.*
J. A. Laramee et al. *Anal. Chem.* 1989, 61, 2154–2160.*

(List continued on next page.)

Primary Examiner—Arlen Soderquist
(74) Attorney, Agent, or Firm—Stephanie L. Seidman; Heller Ehrman White & McAuliffe, LLP

(57) ABSTRACT

Mass spectrometry of large nucleic acids by infrared Matrix-Assisted Laser Desorption/Ionization (MALDI) using a liquid matrix is reported.

30 Claims, 3 Drawing Sheets

U.S. PATENT DOCUMENTS

| | | | |
|---|---|---|---|
| 4,779,467 A | 10/1988 | Rainin et al. | 73/864.17 |
| 4,797,355 A | 1/1989 | Stabinsky | 435/6 |
| 4,798,706 A | 1/1989 | Brigati | 422/102 |
| 4,806,546 A | 2/1989 | Carrico et al. | 536/27 |
| 4,844,298 A | 7/1989 | Ohoka et al. | 222/58 |
| 4,855,225 A | 8/1989 | Fung et al. | 435/6 |
| 4,877,745 A | 10/1989 | Hayes et al. | 436/166 |
| 4,882,127 A | 11/1989 | Rosenthal et al. | 422/50 |
| 4,902,481 A | 2/1990 | Clark et al. | 422/101 |
| 4,920,264 A | 4/1990 | Becker | 250/282 |
| 4,925,629 A | 5/1990 | Schramm | 422/82.05 |
| 4,931,400 A | 6/1990 | Jitsukawa | 435/287 |
| 4,948,442 A | 8/1990 | Manns | 156/73.1 |
| 4,948,882 A | 8/1990 | Ruth | 536/27 |
| 4,952,518 A | 8/1990 | Johnson et al. | 436/518 |
| 4,983,521 A | 1/1991 | Lingappa et al. | 435/172.3 |
| 4,994,373 A | 2/1991 | Stavrianopoulos et al. | 435/6 |
| 5,000,921 A | 3/1991 | Hanaway et al. | 422/100 |
| 5,003,059 A | 3/1991 | Brennan | 536/27 |
| 5,023,187 A | 6/1991 | Koebler et al. | 436/180 |
| 5,045,694 A | 9/1991 | Beavis et al. | 250/287 |
| 5,047,215 A | 9/1991 | Manns | 422/101 |
| 5,062,935 A | 11/1991 | Schlag et al. | 204/157.41 |
| 5,064,754 A | 11/1991 | Mills | 435/6 |
| 5,077,210 A | 12/1991 | Eigler et al. | 435/176 |
| 5,082,935 A | 1/1992 | Cruickshank | 536/27 |
| 5,108,703 A | 4/1992 | Pfost et al. | 422/65 |
| 5,118,937 A | 6/1992 | Hillenkamp et al. | |
| 5,135,870 A | 8/1992 | Williams et al. | 436/86 |
| 5,149,625 A | 9/1992 | Church et al. | 435/6 |
| 5,160,840 A | 11/1992 | Vestal | 250/287 |
| 5,171,989 A | 12/1992 | Williams et al. | 250/288 |
| 5,195,657 A | 3/1993 | Wells | 222/330 |
| 5,202,561 A | 4/1993 | Giessmann et al. | 250/281 |
| 5,210,412 A | 5/1993 | Levis et al. | 250/288 |
| 5,221,518 A | 6/1993 | Mills | 422/62 |
| 5,234,824 A | 8/1993 | Mullis | 435/91 |
| 5,237,016 A | 8/1993 | Ghosh et al. | 525/329.4 |
| 5,242,974 A | 9/1993 | Holmes | 525/54.11 |
| 5,262,128 A | 11/1993 | Leighton et al. | 422/100 |
| 5,283,342 A | 2/1994 | Gustavson et al. | 548/304.1 |
| 5,288,644 A | 2/1994 | Beavis et al. | |
| 5,312,233 A | 5/1994 | Tanny et al. | 417/316 |
| 5,338,688 A | 8/1994 | Deeg et al. | 436/180 |
| 5,373,156 A | 12/1994 | Franzen | 250/288 |
| 5,376,788 A | 12/1994 | Standing et al. | 250/287 |
| 5,380,833 A | 1/1995 | Urdea | 536/22.1 |
| 5,381,008 A | 1/1995 | Tanner et al. | 250/288 |
| 5,382,793 A | 1/1995 | Weinberger et al. | 250/288 |
| 5,410,068 A | 4/1995 | Coull et al. | 548/545 |
| 5,430,136 A | 7/1995 | Urdea et al. | 536/243 |
| 5,436,327 A | 7/1995 | Southern et al. | 536/25.34 |
| 5,439,649 A | 8/1995 | Tseung et al. | 422/99 |
| 5,457,041 A | 10/1995 | Ginaven et al. | 435/172.1 |
| 5,474,895 A | 12/1995 | Ishii et al. | 435/6 |
| 5,478,893 A | 12/1995 | Ghosh et al. | 525/329.4 |
| 5,484,701 A | 1/1996 | Cocuzza et al. | 435/6 |
| 5,492,817 A | 2/1996 | Thompson et al. | 435/68.1 |
| 5,498,545 A | 3/1996 | Vestal et al. | |
| 5,503,980 A | 4/1996 | Cantor | 435/6 |
| 5,506,348 A | 4/1996 | Pieles | 536/23.1 |
| 5,510,613 A | 4/1996 | Reilly et al. | 250/287 |
| 5,512,295 A | 4/1996 | Kornberg et al. | 424/450 |
| 5,512,439 A | 4/1996 | Hornes et al. | 435/6 |
| 5,514,548 A | 5/1996 | Krebber et al. | 436/6 |
| 5,527,675 A | 6/1996 | Coull et al. | 435/6 |
| 5,541,313 A | 7/1996 | Ruth | 536/24.3 |
| 5,545,539 A | 8/1996 | Miller | 435/91.2 |
| 5,547,835 A | 8/1996 | Köster | 435/6 |
| 5,580,733 A | 12/1996 | Levis et al. | 435/6 |
| 5,589,136 A | 12/1996 | Northrup et al. | 422/102 |
| 5,599,500 A | 2/1997 | Jones | 422/62 |
| 5,601,982 A | 2/1997 | Sargent et al. | 435/6 |
| 5,604,099 A | 2/1997 | Erlich et al. | 435/6 |
| 5,605,662 A | 2/1997 | Heller et al. | 422/68.1 |
| 5,605,798 A | 2/1997 | Köster et al. | 435/6 |
| 5,612,474 A | 3/1997 | Patel | 536/27.14 |
| 5,622,824 A | 4/1997 | Köster | 435/6 |
| 5,622,829 A | 4/1997 | King et al. | 435/6 |
| 5,624,711 A | 4/1997 | Sundberg et al. | 427/261 |
| 5,625,184 A | 4/1997 | Vestal et al. | |
| 5,627,369 A | 5/1997 | Vestal et al. | |
| 5,631,134 A | 5/1997 | Cantor | 435/6 |
| 5,641,959 A | 6/1997 | Holle et al. | 250/287 |
| 5,643,722 A | 7/1997 | Rothschild et al. | 435/6 |
| 5,643,798 A | 7/1997 | Beavis et al. | 436/94 |
| 5,654,545 A | 8/1997 | Holle et al. | 250/287 |
| 5,663,242 A | 9/1997 | Gosh et al. | 525/329.4 |
| 5,670,322 A | 9/1997 | Eggers et al. | 435/6 |
| 5,670,381 A | 9/1997 | Jou et al. | 436/518 |
| 5,677,195 A | 10/1997 | Winkler et al. | 436/518 |
| 5,691,141 A | 11/1997 | Köster | 435/6 |
| 5,691,194 A | 11/1997 | Gordon | 435/287.1 |
| 5,700,642 A | 12/1997 | Monforte et al. | 435/6 |
| 5,705,813 A | 1/1998 | Apffel et al. | |
| 5,716,825 A | 2/1998 | Hancock et al. | |
| 5,742,049 A | 4/1998 | Holle et al. | 250/282 |
| 5,743,960 A | 4/1998 | Tisone | 118/683 |
| 5,746,373 A | 5/1998 | Sanada | 239/102.2 |
| 5,756,050 A | 5/1998 | Ershow et al. | 422/100 |
| 5,757,392 A | 5/1998 | Zhang | 347/14 |
| 5,760,393 A | 6/1998 | Vestal et al. | 250/282 |
| 5,777,324 A | 7/1998 | Hillenkamp | 250/288 |
| 5,777,325 A | 7/1998 | Weinberger et al. | 250/287 |
| 5,795,714 A | 8/1998 | Cantor et al. | 435/6 |
| 5,807,522 A | 9/1998 | Brown et al. | 422/50 |
| 5,830,655 A | 11/1998 | Monforte et al. | 435/6 |
| 5,864,137 A | 1/1999 | Becker et al. | 250/287 |
| 5,869,240 A | 2/1999 | Patterson | 435/6 |
| 5,869,242 A | 2/1999 | Kamb | 435/6 |
| 5,872,003 A | 2/1999 | Köster | 435/283.1 |
| 5,885,775 A | 3/1999 | Haff et al. | 435/6 |

FOREIGN PATENT DOCUMENTS

| | | |
|---|---|---|
| EP | 0456304 | 11/1991 |
| EP | 0500506 | 8/1992 |
| EP | 0655501 | 5/1995 |
| EP | 0701001 | 3/1996 |
| FR | 2597260 | 10/1987 |
| GB | 2017105 | 3/1979 |
| JP | 63230086 | 9/1988 |
| JP | 2215399 | 8/1990 |
| JP | 6294796 | 10/1994 |
| JP | 8290377 | 11/1996 |
| WO | 8402579 | 7/1984 |
| WO | 8909282 | 10/1989 |
| WO | 8909406 | 10/1989 |
| WO | 8910786 | 11/1989 |
| WO | 8911270 | 11/1989 |
| WO | 8912694 | 12/1989 |
| WO | 9001564 | 2/1990 |
| WO | 9003382 | 4/1990 |
| WO | 9007582 | 7/1990 |
| WO | 9014148 | 11/1990 |
| WO | 9015883 | 12/1990 |
| WO | 9106678 | 5/1991 |
| WO | 9113075 | 9/1991 |
| WO | 9115600 | 10/1991 |
| WO | 9203575 | 3/1992 |
| WO | 9207879 | 5/1992 |
| WO | 9210092 | 6/1992 |

| WO | 9213629 | 8/1992 |
| WO | 9215712 | 9/1992 |
| WO | 9306925 | 4/1993 |
| WO | 9309668 | 5/1993 |
| WO | 9320236 | 10/1993 |
| WO | 9400562 | 1/1994 |
| WO | 9411529 | 5/1994 |
| WO | 9411530 | 5/1994 |
| WO | 9411735 | 5/1994 |
| WO | 9416101 | 7/1994 |
| WO | 9421822 | 9/1994 |
| WO | 9504524 | 2/1995 |
| WO | 9507361 | 3/1995 |
| WO | 9513538 | 5/1995 |
| WO | 9515001 | 6/1995 |
| WO | 9530773 | 11/1995 |
| WO | 9531429 | 11/1995 |
| WO | 9619587 | 6/1996 |
| WO | 9629431 | 9/1996 |
| WO | 9632504 | 10/1996 |
| WO | 9636731 | 11/1996 |
| WO | 9636732 | 11/1996 |
| WO | 9636986 | 11/1996 |
| WO | 9636987 | 11/1996 |
| WO | 9637630 | 11/1996 |
| WO | 9703499 | 1/1997 |
| WO | 9708306 | 3/1997 |
| WO | 9716699 | 5/1997 |
| WO | 9733000 | 9/1997 |
| WO | 9737041 | 10/1997 |
| WO | 9742348 | 11/1997 |
| WO | 9743617 | 11/1997 |
| WO | 9803684 | 1/1998 |
| WO | 9812355 | 3/1998 |
| WO | 9820019 | 5/1998 |
| WO | 9820020 | 5/1998 |
| WO | 9820166 | 5/1998 |
| WO | 9826095 | 6/1998 |
| WO | 9854751 | 12/1998 |
| WO | 9912040 | 3/1999 |
| WO | 9914375 | 3/1999 |

OTHER PUBLICATIONS

M. Takayama *Org. Mass Spectrom*, 1991, 26, 1123–1124.*
T. W. Chan et al. Org. Mass Spectrom. 1992, 27, 53–56.*
K. Jiang et al. Chin. Sci Bull. 1992, 37, 1431–1435.*
P. Y. Yau et al. *Chem. Phys. Lett.* 1993, 202, 93–100.*
D. Cornett et al. *Anal. Chem.* 1993, 65, 2608–2613.*
Y. L. Kim et al. *Mikrochim, Acta* 1994, 113, 101–111.*
D. Fabris et al. *J. Mass Spectrom*, 1995, 30, 140–143.*
M. Wolter et al, *J. Mass Spectrom.* 1995, 30, 485–491.*
J. M. Hunter et al. *Proc. SPIE—Int. Soc. Opt. Eng.* 1996, 2680, 384–389.*
V. S. K. Kolli et al. *Rapid Commun. Mass Spectrom.* 1996, 10, 923–926.*
M. J. Dale et al. *Anal. Chem.* 1996, 68, 3321–3329.*
V. Kovacik et al. Rapid Commun. Mass Spectrom, 1996, 10, 1661–1667.*
K. O. Bornsen et al. Rapid Commun. Mass Spectrom. 1997, 11, 603–609.*
M. M. Siegel et al. *Anal. Chem.* 1997, 69, 2716–2726.*
T. L. Williams et al. *Eur. Mass Spectrom.* 1998, 4, 379–383.*
Clark et al., Experimenting in picoliter microvials, *CHEMTECH* 28: 20–25 (1998).
Ferstenau and Benner, Molecular weight determination of megadalton DNA electrospray ions using charge detection time–of–flight mass spectrometry, *Rapid Commun. Mass Spectrom.* 9:1528–1538 (1995).

Gruic–Sovolj et al., Detection of noncovalent tRNA–aminoacyl–tRNA synthetase complexes by matrix–assisted laser desorption/ionization mass spectrometry, *J. of Biol. Chem.* 1997, 272, 32084–91.
Hahner et al. Matrix–Assisted Laser Desorption/Ionization Mass Spectrometry (MALDI) of Endonuclease Digests of RNA, *Nucleic Acid Research*, v. 25, 10:1957–1964 (1997).
Jespersen et al. (1996) p. 217 in *Mass Spectrom. in Biol. Sci*, Burlingame, Ed.).
Lecchi et al. *J. Am. Soc. Mass Spectrom.* 1995, 6, 972–75.
McLaffery et al., High–resolution tandem FT mass spectrometry above 10 kDa, *Acc. Chem. Res.* 27:297–386 (1994).
Nordoff E., Matrix–Assisted Laser Desorption/Ionization Mass Spectrometry as a new method for the characterization of nucleic acids, *Trac, Trends in Analytical Chemistry, GB, Analytical Chemistry*, v. 15, 6:240–250 (1996).
Overberg et al., Matrix–Assisted Laser Desorption Mass Spectrometry: A Sensitive Technique for the Analysis of Macromolecules, *Laser und Optoelectronik Fuer Makromolekuele*, v. 24, 1:50–58 (1992).
*Protein LabFax*, ed., N.C. Price; Bios Scientific Publ. pp. 273–276 (1996).
Spengler et al., Fundamental aspects of postsource decay in matrix–assisted laser desorption mass spectrometry, *J. Phys. Chem.* 96:9678–9684 (1992).
Vestal et al., Delayed extraction matrix–assisted laser desorption time–of–flight mass spectrometry, *Rapid Commun. Mass Spectrom.* 9:1044–1050 (1995).
Siegel et al., Calicheamicin derivatives conjugated to monoclonal antibodies: determination of loading values and distributions by infrared and UV matrix–assisted laser desorption/ionization mass spectrometry and electrospray ionization mass spectrometry, *Anal. Chem.* 69:2716–2726 (1997).
Overberg, A., et al. "Matrix–assisted Infrared–Laser (2.94um) Desorption/Ionization Mass Spectrometry of Large Biomolecules" Rapid Communications in Mass–Spectrometry vol. 4, p. 293 (1990).
Overberg, A., et al. "Matrix–assisted Laser Desorption of Large Biomolecules with a TEA–$CO_2$–Laser" Rapid Communications in Mass Spectrometry, vol. 5, No. 3, pp. 128–131 (1991).
Nordhoff, E., et al. "Matrix–assisted Laser Desorption/Ionization Mass Spectrometry of Nucleic Acids with Wavelengths in the Ultraviolet and Infrared" Rapid Communications in Mass Spectrometry vol. 6, pp. 771–776 (1992).
Nordhoff, E., et al. "Ion stability of nucleic acids in infrared matrix–assisted laser desorption/ionization mass spectrometry" Nucleic Acids Research, vol. 21, No. 15 pp. 3347–3357, (1993).
Nordhoff, E., et al. "Direct Mass Spectrometric Sequencing of Low–picomole Amounts of Oligodeoxynucleotides with up to 21 Bases by Matrix–assisted Laser Desorption/Ionization Mass Spectrometry" Journal of Mass Spectrometry, vol. 30, pp. 99–112 (1995).
Ross, P., et al. "Analysis of Short Tandem Repeat Polymorphisms in Human DNA by Matrix Assisted Laser Desorption/Ionization Mass Spectrometry" Anal. Chem, vol. 69, pp. 3966–3972 (1997).
Agrawal et al., Efficient methods for attaching non–radioactive labels to the 5' ends of synthetic oligodeoxyribonucleotides, *Nucleic Acids Res. 14*:6227–6245 (1986).

Alderton et al., Magnetic bead purification of M13 DNA sequencing templates, *Anal. Biochem.* 201:166–169 (1992).

Alimpiev et al., Laser desorption mass spectrometry from frozen water solutions using a 3.28 μm YAG/OPO laser system, Proceedings from the 44th ASMS Conference on Mass Spectrometry, p. 644.

Andersen, et al., Electrospray ionization and matrix assisted laser desorption/ionization mass spectrometry: Powerful analytical tools in recombinant protein chemistry, *Nature Biotech.* 14:449–457 (1996).

Ardey, Electrospray mass spectrometry, *Spectroscopy Europe,* 4:10–20 (1992).

Arlinghaus et al., "Applications of resonance ionization spectroscopy for semiconductor, environmental and biomedical analysis, and for DNA sequencing", SPIE, vol. 1435, *Opt. Methods Ultrasensitive Detect. Anal. Tech. Appl.* pp. 26–35 (1991).

Arshady, Reza; Review: Beaded Polymer Supports and Gels, I. Manufacturing Techniques; Journal of Chromatography, 586 (1991); pp. 181–197.

Arshady, Reza, Beaded polymer supports and gels: II. Physico–chemical criteria and functionalization, *Journal of Chromatography,* 586:199–219 (1991).

Bai et al., Procedures for detection of DNA by matrix–assisted laser desorptioin/ionization mass spectrometry using a modified nafion film substrate, *Rapid Comm. Mass Spectrom* 9:1172–1176 (1995).

Bains, Setting a sequence to sequence a sequence, *Biotechnology* 10:757–758 (1992).

Bains, DNA Sequencing by mass spectrometry: Outline of a potential future application, *Chimicaoggi* 9:13–16 (1991).

Bannwarth, Solid–phase synthesis of oligodeoxynucleotides containing phosphoramidate internucleotide linkages and their specific chemical cleavage, *Helvetica Chimica Acta* 71:1517–1527 (1988).

Barany F., Genentic disease detection and DNA amplification using cloned thermostable ligase, *Proc. Natl. Acad. Sci.* 88:189–193 (1991).

Barrell B., "DNA sequencing: present limitations and prospects for the future", *FASEB Journal* 5:40–45 (1991).

Batista–Viera et al., A new method for reversible immobilization of thiol biomolecules bsed on solid–phase bound thiolsulfonate groups, *App. Biochem and Biotech,* 31:175–195 (1991).

Beaucage et al., The synthesis of modified oligonucleotides by the phosphoramidite approach and their applications, *Tetrahedron* 49:6123–6194 (1993).

Beck et al., Applications of dioxetane chemiluminescent probes to molecular biology, *Anal. Chem.* 62:2258–2270 (1990).

Beck et al., Chemiluminescent detection of DNA: application for DNA sequencing and hybridization, *Nucl Acids Res* 17:5115–5123 (1989).

Berkenkamp et al., Infrared MALDI mass spectrometry of large nucleic acids, *Science* 281:260–2 (1998).

Berkenkamp et al., Performance of infrared matrix–assisted laser desorption/ionization mass spectrometry with lasers emitting in the 3 μm wavelength range, *Rapid Commun. Mass Spectrom.* 11:1399–1406 (1997).

Berkenkamp et al., Water as a matrix in infrared MALDI–MS, Proceedings of the 43rd ASMS Conference on Mass Spectrometry and Allied Topics, p. 1247, Atlanta, Georgia, May 1995.

Berkenkamp et al., Infrared MALDI–MS of large nucleic acids, Proceedings of the 46th ASMS Conference on Mass Spectrometry and Allied Topics, Orlando, Florida, May 31–Jun. 4, 1998.

Berkenkamp et al., Ice as a matrix for IR–matrix–assisted laser desorption/ionization: mass spectra from a protein single crystal, *Proc. Natl. Acad. Sci. USA* 93:7003–7007 (1996).

Braun et al., "Improved Analysis of Microsatellites Using Mass Spectrometry", *Genomics* 46:18–23 (1997).

Braun et al., Detecting CFTR gene mutations by using primer oligo base extension and mass spectrometry, *Clinical Chemistry 43*: 1151–1158 (1997).

Brennan et al., New methods to sequence DNA mass spectrometry, *SPIE*, vol. 1206, *New Technol. Cytom. Mol. Biol.* pp. 60–77 (1990).

Broude, Natalia E. et al., "Enhanced DNA Sequencing by hybridization (streptavidin/biotin/stacking interaction/T4 DNA ligase/DNA polymerase)", *Proc. Natl. Acad. Sci.,* 91:3072–3076 (1994).

Brown, et al., "A single–bead decode strategy using electrospray ionization mass spectrometry and a new photolabile linker: 3–amino–3–(2–nitrophenyl) propionic acid", *Mol. Diversity* 1:4–12(1995).

Caldwell et al., Mid–infrared matrix assisted laser desorption ionization with a water/glycerol matrix, *Applied Surface Science* 127–127:242–247 (1998).

Chait and Kent, Weighing naked proteins: practical, high–accuracy mass measurement of peptides and proteins, *Science* 257:1885–1894 (1992).

Charkrabarti et al., Sequence of Simian Immunodeficiency Virus from Macaque and its Relationship to Other Human and Simian Retroviruses, Nature 328:543–547 (1987).

Chen and Seeburg, Supercoil sequencing: A fast and Simple method for sequencing plasmid DNA, *DNA* 4(2):165–170 (1985).

Chen et al., Trapping, detection, and mass determination of coliphage T4 DNA ions of $10^8$ DA by electrospray ionization fourier transform ion cyclotron resonance mass spectrometry, *Anal. Chem.* 67:1159–1163 (1995).

Chrisey et al., Covalent attachment of synthetic DNA to self assembled monlayer films, *Nucl. Acids Res.* 24:3031–3039 (1996).

Chrisey et al., Fabrication of patterned DNA surfaces, *Nucl. Acids. Res.* 24:3040–3047 (1996).

Church et al., "Multiplex DNA Sequencing", *Science* 240:185–188 (1988).

Connolly, B. A., "Oligonucleotides containing modified bases", *Oligonucleotides and Analogues, A Practical Approach,* Edited by F. Eckstein, Oxford University Press, Ch. 7, pp. 40–45 (1991).

Covey, et al., The determination of protein, oligonucleotide and peptide molecular weights by ion–spray mass soectrometry, *Rapid Comm. Mass Spectrom.* 2:249–256 (1988).

Crain, Mass spectrometric techniques in nucleic acid research, *Mass Spectrom. Rev.* 9:505–554 (1990).

Cramer et al., Analysis of Phospho– and glycopolypeptides with infrared matrix–assisted laser desorption and ionization, *Anal. Chem.* 70:4939–4944 (1998).

Damha, Masad J. et al., An improved procedure for derivatization of controlled–pore glass beads for solid–phase oligonucleotide synthesis; *Nucleic Acids Research* 18(13):3813–3821 (1990).

Drmanac, et al., "Sequencing of megabase plus DNA by hybridization: theory of the method", *Genomics* 4:114–128 (1989).

Eckerskorn et al., High Sensitivity peptide mapping by micro–LC with on–line membrane blotting and subsequent detection by scanning–IR–MALDI mass spectrometry, *J of Protein Chem* 16(5):349–362 (1997).

Eckstein and Goody, Synthesis and properties of diastereoisomers of adenosine 5'–(O–1–thiotriphosphate) and adenosine 5'–(O–2–thiotriphosphate), *Biochemistry* 15(8):1685–1691 (1976).

Eckstein, Nucleoside phosphorothioates, *Ann. Rev. Biochem.* 54:367–402 (1985).

Eckstein, F., Phosphorothioate analogues of nucleotides, *Accounts Chem. Res.* 12:204–210(1979).

Edmonds et al., Thermospray liquid chromatography–mass spectrometry of nucleosides and of enzymatic hydrolysates of nucleic acids, *Nucleic Acids Research* 13:8197–8206 (1985).

Eggers et al., "A microchip for quantitative detection of molecules utilizing luminescent and radioisotope reporter groups", *Bio Techniques* 17:516–524 (1994).

Ehring et al., Photochemical versus thermal mechanisms in matrix–assisted laser desorption/ionization probed by back side desorption, *Rapid Comm in Mass Spect* 10:821–824 (1996).

Eperon, I. C., Rapid preparation of bacteriophage DNA for sequence analysis in sets of 96 clones, using filtration, *Anal. Biochem* 156:406–412 (1986).

Fenn, et al., Electrospray ionization for mass spectrometry of large biomolecules, *Science* 246:64–71 (1989).

Ferrie et al., Development, multiplexing, and application of ARMS tests for common mutations in the CFTR gene, *Am. J. Hum. Genet.* 51:251–262 (1992).

Frank and Köster, DNA chain length and the influence of base composition on electrophoretic mobility of oligodeoxyribonucleotides in polyacrylamide–gels, *Nucl. Acids Res.* 6:2069–2087 (1979).

Fu, et al., "A DNA sequencing strategy that requires only five bases of known terminal sequence for priming (primer extention/stacking interaction/fluorescein/solid state/duplex probe)", *Proc. Natl. Acad. Sci. USA* 92:10162–10166 (1995).

Fu et al., Sequencing exons 5 to 8 of the p53 gene by MALDI–TOF mass spectrometry, *Nat Biotechnol* 16:381–4 (1998).

FU et al., Efficient preparation of short DNA sequence ladders potentially suitable for MALDI–TOF DNA sequencing, *Genetic Analysis* 12:137–142 (1996).

Fu et al., Sequencing double–stranded DNA by strand displacement, *Nucl Acids Res* 25:677–679 (1997).

Fu et al., A DNA sequencing strategy that requires only five bases of known terminal sequenec for priming, *Proc. Natl. Acad. Sci. USA* 92:10162–10166 (1995).

Fu et al., A DNA sequencing strategy which requires only five bases of known terminal sequence for priming, Paper presented, Genome Mapping and Sequencing, Cold Spring Harbor Laboratory.

Fuerstenau & Brenner, Molecular weight determination of megadalton DNA electrospray ions using charge detection time–of–flight mass spectrometry, *Rapid Comm. Mass Spectrom.* 9:1159–1163 (1995).

Fujita et al., Surprising lability of biotin–streptavidin bond during transcription of biotinylated DNA bound to paramagnetic beads, *BioTechniques* 14:608–617 (1993).

Ganem et al., Detection of oligonucleotide duplex forms by ion–spray mass spectrometry, *Tetrahedron Letters* 34:1445–1448, (1993).

Ghosh, et al., "Covalent attachment of oligonucleotides to solid supports", *Nuc. Acids. Res.* 15)13):5353–5372 (1987).

Gildea et al., A versatile acid–labile linker for modification of synthetic biomolecules, *Tetrahedron Letters* 31:7095–7098 (1990).

Goldmacher et al., Photoactivation of toxin conjugates, *Bioconjugate Chem.* 3:104–107, (1992).

Gross et al., Investigations of the metastable decay of DNA under ultraviolet matrix–assisted laser desorption/ionization conditions with post–source–decay analysis and hydrogen/deuterium exchange, *J Amer Soc for Mass Spect* 9:866–878 (1998).

Gruić–Sovulj I. et al., Matrix–assisted laser desorption/ionisation mass spectrometry of transfer ribonucleic acids isolated from yeast, *Nucleic Acids Res.* 25(9):1859–61 (1997).

Gust et al., Taxomonic classifcation of Hepatitis A virus *Intervirology* 20:1–7 (1983).

Guyader, et al., "Genome organization and transactivation of the human immunodeficiency virus type 2", *Nature* 326:662–669 (1987).

Haglund et al., Matrix–assisted laser–desorption mass spectrometry of DNA using an infrared free–electron laser, *SPIE* 1854:117–128 (1993).

Hayashi, et al., "Immobilization of Thiol Proteases onto porous poly(vinyl alcohol) beads", *Polymer Journal*, 25(5):489–497 (1993).

Hazum et al., A photocleavable protecting group for the thiol function of cysteine, *Pept., Proc. Eur. Pept. Symp., 16th*, Brunfeldt, K (ed), pp. 105–110 (1981).

Heermann, et al., "Liquid–phase hybridization and capture of hepatitis B virus DNA with magnetic beads and fluorescence detection of PCR product", *J. of Virol. Methods* 50:43–58 (1994).

Higuchi et al., A general method of in vitro preparation and mutagenesis of DNA fragments: Study of protein and DNA interactions, *Nucleic Acids Res.* 16:7351–7367 (1988).

Higuchi et al., Kinetic PCR analysis: Real–time monitoring of DNA amplification reactions, *Bio/Technology* 11:1026–1030 (1993).

Hillenkamp et al., Matrix Assisted UV–Laser Desorption/Ionization: A New Approach to Mass Spectrometry of Large Biomolecules, *Biological Mass Spectrometry*, Editors: A. L. Burlingame and J. A. McCloskey, Elsevier Science Publishers, B. V., Amsterdam, pp. 49–61 (1989).

Hillenkamp et al., MALDI–MS in the infrared: a critical evaluation, Proceedings of the 43rd ASMS Conference on Mass Spectrometry and Allied Topics, p. 357, Atlanta, Georgia, May 1995.

Hillenkamp and Ehring, Laser desorption mass spectrometry Part 1: Basic mechanisms and techniques, *Mass Spectrometry in the Biological Sciences: A tutorial*, (1992), 165;167;169;171;173;175;177 & 179.

Hillenkamp, et al., Matrix assisted UV–laser desorption/ionization: A new approtach to mass spectrometry of large biomolecules, In *Biological Mass Spectrometry* (Burlingame and McCloskey, eds.), Elsevier, Amsterdam (1989).

Hillenkamp and Karas, Matrix–assisted laser desorption/ionization mass spectrometry of biopolymers, *Anal. Chem* 63(24):1193–1203 (1991).

Hillenkamp, MALDI–MS with other wavelengths: options, potentials and limitations, Proceedings of the 46th ASMS Conference on Mass Spectrometry and Allied Topics, Oraldno, Florida, p. 796, May 31–Jun. 4, 1998.

Hobbs and Eckstein, A general method for the synthesis of 2'–azido–2'deoxy–and 2'–amino–2'–deoxyribofuranoxyl purines, *J. Org. Chem. 42*:714–719 (1976).

Hopert et al., Specifity and sensitivity of polymerase chain reaction (PCR) in comparison with other methods for the detection of mycoplasma contamination in cell lines, *J. Immunol. Methods* 164:91–100 (1993).

Hornes and Korsnes, Magnetic DNA hybridization of oligonucleotide probes attached to superparamagnetic beads and their use in the isolation of Poly(A) mRNA from eukaryotic cells, *GATA* 7:145–150, (1990).

Hsiung et al., A new simpler photoaffinity analogue of peptidyl rRNA, *Nucl Acids Res 1*:1753–1762 (1974).

Hultman et al., Direct solid phase sequencing of gemonic and plasmind DNA using magnetic beads as solid support, *Nucl. Acids Res. 17*:4937–4946 (1989).

Huth–Fehre et al., Matrix–assisted laser desorption mass spectrometry of oligodeoxythymidylic acids, *Rapid Comm in Mass Spect 6*:209–213 (1992).

Hyman, A new method of sequencing DNA, *Anal. Biochem. 174*:423–436 (1988).

Innis et al., DNA sequencing with *Thermus aquaticus* DNA polymerase and direct sequencing of polymerase chain reaction–amplified DNA, *Proc. Natl. Acad. Sci. USA* 85:9436–9440 (1988).

Jacobson, et al. Applications of mass spectrometry to DNA sequencing, *GATA 8*:223–229 (1991).

Jett et al., "High–Speed DNA Sequencing: An approach Based Upon fluorescence Detection of Single Molecules", *J. Bio Strut & Dynam. 7*(2)301–09 (1989).

Ji et al., Two–dimensional electrophoretic analysis of proteins expressed by normal and cancerous human crypts: Application of mass spectrometry to peptide–mass fingerprinting, *Electrophoresis* 15:391–405 (1994).

Juhasz et al., Applications of delayed extraction matrix–assisstes laser desorption ionization time–of–flight mass spectrometry to oligonucleotide analysis, *Analy Chem* 68:941–946 (1996).

Jurinke et al., Analysis of ligase chain reaction products via matirx–assisted laser desorption/ionization time–of–flight–mass spectrometry, *Analy Biochem 237*:174–181 (1996).

Jurinke et al., Application of nested PCR and mass spectrometry for DNA–based virus detection: HBV–DNA detected in the majority of isolated anti–HBc positive sera, *Genetic Analysis 14*:97–102 (1998).

Jurinke et al., Recovery of nucleic acids from immobilized biotin–streptavidin complexes using ammonium hydroxide and applications in MALDI–TOF mass spectrometry, *Anal. Chem. 69*:904–910 (1997).

Jurinke et al., Detection of hepatitis B virus DNA in serum samples via nested PCR and MALDI–TOF mass spectrometry, *Genetic Analysis 13*:67–71 (1996).

Karas & Hillenkamp, Laser desorption ionization of proteins with molecular masses exceeding 10 000 daltons, *Anal. Chem.* 60:2299–3001 (1988).

Khrapko et al., An oligonucleotide hybridization approach to DNA sequencing, *FEB* 256(1,2):118–122 (1989).

Khrapko et al., "A method for DNA sequencing by hybridization with oligonucleotide matrix", *J. DNA Seq. and Mapping* 1:375–388 (1991).

Kirkepar et al., Matrix Assisted Laser Desorption/Ionization Mass Spectrometry of Enzymatically Synthesized RNA up to 150 kDa, Nucl. Acids Res. 22:3866–3870 (1994).

Kirpekar et al., "7–deaza purine bases offer a higher ion stability in the analysis of DNA by matrix–assisted laser desorption/ionization mass spectrometry" *Rapid Commun. Mass Spectrom. 9*:525–531 (1995).

Kirpekar et al., Double stranded DNA analysed by UV–and IR–MALDI–MS, Proceedings of the 46th ASMS Conference on Mass Spectrometry and Allied Topics, p. 1004, Orlando, Florida, May 31–Jun. 4, 1998.

Kirpekar et al., DNA sequence analysis by MALDI mass spectrometry, *Nucleic Acids Res. 26*:2554–9 (1998).

Köster et al., Polymer support oligonucleotide synthesi—XV$^{1,2}$, *Tetrahedron 40*:102–112 (1984).

Köster et al., Some improvements in the synthesis of DNA of biological interest, *Nucl Acids Res 7*:39–59 (1980).

Köster et al., Well defined insoluble primers for the enzymatic synthesis of oligo– and polynucleotides, *Hoppe–Seyler's Z. Physiol. Chem. 359*:11579–1589 (1978).

Köster et al., "Oligonucleotide synthesis and multiplex DNA sequencing using chemiluminescent detection", *Nucleic Acids Research*, Symposium Series No. 24, 318–321 (1991).

Köster et al., N–acyl protecting groups for deoxynucleotides: A quantitative and comparative study, *Tetrahedron 37*:363–369 (1981).

Köster et al., "A strategy for rapid and efficient DNA sequencing by mass spectrometry", *Nature Bio 14*:1123–1128 (1996).

Kozal et al., "Extensive polymorphisms observed in HIV–1 clade B protease gene using high–density oligonucleotide arrays", *Nature Medicine*, 2(7):753–759 (1996).

Kuppuswamy, et al., "Single nucleotide primer extension to detect gentic diseases: experimental application to hemophilia B (factor IX) and cystic fibrosis genes", *Proc. Natl. Acad. Sci. USA* 88:1143–1147 (1991).

Kussman et al., Matrix–assisted Laser Desorption /Ionization Mass Spectrometry Sample Preparation Techniques Designed for Various Peptide and Protein Analytes, J. Mass Spectrom. 32:593–601 (1997).

Labeit et al., Laboratory methods: A new method of DNA sequencing using deoxynucleoside α–thiotriphophates, *DNA* 5:173–177 (1986).

Lamture et al., "Direct detection of nucleic acid hybridization on the surface of a charge coupled device", *Nucl. Acids Res.* 22:2121–2125 (1994).

Landegren et al., "DNA Diagnostics—Molecular techniques and automation", *Science* 242:229–237 (1988).

Lawrance et al., Megabase–scale mapping of the HLA gene complex by pulsed field gel electrophoresis, *Science 235*:1387–1389 (1987).

Li et al., "Analysis of single mammalian cell lysates by mass spectrometry", *J. Am. Chem. Soc.* 118:11662–11663 (1996).

Li et al., "High–Resolution MALDI Fourier Transform Mass Spectrometry of Oligonucleotides", *Anal Chem 68*(13):2090–2096 (1996).

Limbach et al., Molecular mass measurement of intact ribonucleic acids via electrospray ionization quadrupole mass spectrometry, *J. Am. Soc. Mass Spectrom* 6:27–39 (1995).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal. chem* 69:4540–4546 (1997).

Little et al., Identification of apolipoprotein E polymorphisms using temperature cycled primer oligo base extension and mass spectrometry, *Short Communication*.

Little et al., "Mass spectrometry from miniaturized arrays for full comparative DNA analysis", *Nature Med* 3(12):1413–1416 (1997).

Little et al., Direct detection of synthetic and biologically generated double–stranded DNA by MALDI–TOF MS, *J. Mass Spec* 17:1–8 (1997).

Little et al., Verification of 50– to 100–mer DNA and RNA sequences with high–resolution mass spectrometry, *Proc. Natl. Acad. Sci. USA* 92:2318–2322 (1995).

Little et al., MALDI on a chip: analysis of arrays of low–femtomole to subfemtomole quantities of synthetic oligonucleotides and DNA diganostic products dispensed by a piezoelectric pipet, *Anal Chem* 69:4540–4546 (1997).

Little et al., Detection of RET proto–oncogene codon 634 mutations using mass spectrometry, *J. Mol Med.* 75:745–750 (1997).

Liu et al., Use of a nitrocellulose film substrate in matrix–assisted laser desorption/ionization mass spectrometry for DNA mapping and screening, *Anal. Chem.* 67:3482–3490 (1995).

Lopez–Galindez, et al., "Characterization of genetic variation and 3'–azido–3'–deoxythymidine–resistance mutations of human immunodeficiency virus by the RNase A mismatch cleavage method", *Proc. Natl. Acad. Sci, USA* 88:4280–4284 (1991).

Lund, Vera et al., "Assessment of methods for covalent binding of nucleic acids to magnetic beads, dynabeads, and the characteistics of the bound nucleic acids in hybridization reactions", *Nucleic Acids Res.* 16(22) (1988).

Manoharan et al., A 2'–O–thiol tether in the ribose moiety of nucleic acids for conjugation chemistry, *Gene*, 149:147–156 (1994).

Marshall and Hodgson, "DNA chips: An array of possibilities", *Nature Biotechnology* 16:27–31 (1998).

Martin, "New technologies for large–genome sequencing", *Genome 31*:1073–1080 (1989).

Matteucci et al., Synthesis of deoxyoligonucleotides on a polymer support, *J. A. Chem. Soc. 103*:3185–3191, 1981.

Matthews, et al., "Analytical strategies for the use of DNA probes", *Analytical Biochemistry* 169:1–25 (1988).

Maxam and Gilbert, Sequencing end–labeled DNA with base–specific chemical cleavages, *Methods in Enzymology* 65:499–560 (1980).

McCray and Trentham, "Properties and uses of photoreactive caged compounds", *Annu. Rev. Biophys. Chem. 18*:239–270 (1989).

Melton et al., Efficient in vitro synthesis of biologically active RNA and RNA hybridization probes from plasmids containing a bacteriophage SP6 promoter, *Nucl. Acids Res.* 12:7035–7056 (1984).

Menzel et al., IR–MALDI–MS in the $3\mu$m wavelength region with lasers of different pulse width, Proceedings of the 46th ASMS Conference on Mass Spectrometry and Allied Topics, Orlando, Florida, p. 922, May 31–Jun. 4, 1998.

Menzel et al., New developments in IR–MALDE–MS with a TEA–$CO_2$–Laser, Proceedings of the 46th ASMS Conference on Mass Spectrometry and Allied Topics, p. 797, Orlando, Florida, May 31–Jun. 4, 1998.

Miyazaki, et al., The first Japanese case of Hb Santa Ana, an unstable abnormal hemoglobin, identified rapidly by electrospray ionization mass spectrometry. *Internal Medicine 36*:365–370 (1997).

Mizusawa, et al., "Improvement of the dideoxy chain termination method of DNA sequencing by use of deoxy–7–deazaguanosine triphosphate in place of dGTP", *Nucleic Acids Res.* 14(3):1319–1325 (1986).

Moini et al., "A Moving Belt Device to Couple High–Performance Liquid Chromatography and Chemical Reaction Interface Mass Spectrometry", *Bio Mass Spect 20*:308–312 (1991).

Monforte and Becker, High–throughput DNA analysis by time–of–flight mass spectrometry, *Nature Medicine 3*:360–362 (1997).

Mosca et al., Mass spectrometry and DNA analysis, *Hemoglobin* 17(3):261–268 (1993).

Muddiman et al., Characterization of PCR products from Bacilli using electrospray ionization FTICR mass spectrometry, *Anal. Chem.* 68:3705–3715 (1996).

Murray, "DNA sequencing by mass spectrometry", *J. Mass. Spect. 31*:1203–1215 (1996).

Nakamaye et al., "Direct sequencing of polymerase chain reaction amplified DNA fragments through the incorporation of deoxynucleoside α–thiotriphosphates", *Nucleic Acids Res.* 16(21):9947–9959 (1988).

Nelson et al., Time–of–flight mass spectrometry of nucleic acids by laser ablation and ionization from a frozen aqueous matrix, *Rapid Communications in Mass Spectrometry* 4:348–351 (1990).

Nelson et al., "Volatilization of High Molecular Weight DNA by Pulsed Laser Ablation of Frozen Aqueous Solutions", *Science 246*:1585–1587 (1989).

Newton et al., "The production of PCR products with 5'single–stranded tails using primers that incorporate novel phosphoramidite intermediates", *Nucl. Acids. Res.* 21:1155–1162 (1993).

Nikiforov et al. "Genetic Bit Analysis: a solid phase method for typing single nucleotide polymorphisms" Nucleic Acids Research, 22(20):4167–4175 (1994).

Nikiforov and Rogers, "The use of 96–well polystyrene plates for DNA hybridization–based assays: An evaluation of different approaches to oligonucleotide immobilization", *Anal. Biochm.* 227:201–209 (1995).

Niu et al., Direct comparison of infrared and ultraviolet wavelength matrix–assisted laser desorption/ionization mass spectrometry of proteins, *J Am Soc Mass Spectrom* 9:1–7 (1998).

Nordhoff et al., Comparison of IR– and UV–matrix–assisted laser desorption/ionization mass spectrometry of oligodeoxynucleotides, *Nuc Acids Res* 22(13):2460–2465 (1994).

Nordhoff, et al., Direct Mass Spectrometric Sequencing of Low–picomole Amounts of Oligodeoxynucleotides with up to 21 Bases by Matrix–assisted Laser Desorption/Ionization Mass Spectrometry, J. Mass Spectrom. 30:99–112 (1995).

Nordhoff, et al., Mass spectrometry of nucleic acids, *Mass Spectrom. Rev.* 15:67–138 (1977).

O'Donnell et al., High–density, covalent attachment of DNA to silioсn wafers for analysis by MALDI–TOF mass spectrometry, *Analytical Chemistry 69*:2438–2443 (1997).

O'Donnell et al., "MassArray as an Enabling Technology for the Industrial–Scale Analysis of DNA", *Genetic Engineering News 17*(21) (1997).

O'Donnell–Maloney et al., Microfabrication and array technologies for DNA sequencing and diagnostics, *Genetic Analysis: Biomolecular Engineering 13*:151–157 (1996).

O'Donnell–Maloney et al., The development of microfabricated arrays for DNA sequencing and analysis, *TIBTECH* 14:401–407 (1996).

Olejnik et al., "Photocleavable biotin phosphoramidite for 5'–end–labeling, affinity purification and phosphorylation of synthetic oligonucleotides", *Nucleic Acids Res.* 24:351–366 (1996).

*Oligonuleotides and Analogues: A Practical Approach*, Eckstein, ed., Oxford University Press Ch. 3, pp. 49–59, 137–139, 255–259 (1991).

Ornstein et al., Sequencing DNA using $^{35}$S–labeling: A troubleshooting guide, *Biotechniques 3*:476–483 (1985).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial 181–197* (1992).

Pieles et al., Matrix–assisted laser desorption ionization time–of–flight mass spectrometry: a powerful tool for the mass and sequence analysis of natural and modified oligonucleotides, *Nucleic Acids Res. 21*:3191–3196 (1993).

Pierce Catalog, pp. T123–T154, 1994.

Pierce ImmunoTechnology Catalog, p. 57 (1993).

Pomerantz et al., Determination of oligonulceotide composition from mass spectrometrically measured molecular weight, *Am. Soc. Mass Spectrom. 4*:204–09 (1993).

Pon, Richard T. et al.; Research Report: Derivatization of Controlled Pore Glass Beads for Solid Phase Oligonucleotide Synthesis; BioTechniques vol. 6, No. 8 (1988); pp. 768–770, 773–775.

Prome et al., Use of combined mass spectrometry methods for the characterization of a new variant of human hemoglobin: The double mutant hemoglobin villeparisis beta 77(EF1), *J. American Society for Mass Spect 7*(2):163–167 (1996).

Raftery, et al., Characterization of a mutant recombinant S100 protein using electrospray ionization mass spectrometry. *Rapid Comm. Mass Spec. 11*:405–409 (1997).

Rasmussen et al., "Covalent immobilization of DNA onto polystyrene microwells: The molecules ar eonly bound at the 5' end", *Anal. Biochem.* 198:138–142 (1991).

Ratner et al., Complete nucleotide sequence of the AIDS virus, HTLV–III, *Nature 313*:227–284 (1985).

Rink, "Solid–phase synthesis of protected peptide fragments using a trialkoxy–diphenyl–methlester resin", *Tetrahedron Lett.* 28:3787–3790 (1987).

Running and Urdea, "A procedure for productive coupling of synthetic oligonucleotides to polystyrene microtiter wells for hybridization capture", *Biotechniques* 8:276–277 (1990).

Ruppert et al., A filtration method for plasmid isolation using microtiter filter plates, *Anal. Biochem.* 230:130–134 (1995).

Ruppert et al., "A rapid and high throughput method for plasmid isolations", Presented: Automation in Mapping and DNA Sequencing Conference, Aug. 31–Sep. 2 1994.

Ruppert et al., "Preparation of plasmid DNA as Sequencing Templates in a Microtiter Plate Format", Paper presented, Cold Spring Harbor Laboratory, N.Y. May 10–14, 1995.

Saiki, et al., "Genetic analysis of amplified DNA with immobilized sequence–specific oligonucleotide probes", *Proc. Natl. Acad. Sci. USA* 86:6230–6234 (1989).

Sanger et al., DNA sequencing with chain–terminating inhibitors, *Proc. Natl. Acad. Sci.* 74:5463–67 (1977).

Sasaki et al., Introduction of an azide group into some uridine derivatives via 2',3'–benzoxonium and 2',3'–azidonium intermediates, *J. Org. Chem. 41*:3138–3143 (1976).

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res. 23*(9):1570–1575 (1995).

Schram, Karl H., "Mass Spectrometry of Nucleic Acid Components", *Bio Appl of Mass Spect. 34*:203–287 (1990).

Seela and Kehne, Palinddromic octa– and dodecanucleotides containing 2'–deoxytubercidin: Synthesis, hairpin formation, and recognition by the endodeoxyribonuclease EcoRI, *Biochemistry 26*:2232–2238 (1987).

Senter et al., Novel photocleavable protein crosslinking reagents and their use in the preparation of antibody–toxin conjugates, Photochem. Photobiol. 42:231–237, (1985).

Sequenom Advances the Industrial Genomics Revolution with the Launch of Its DNA MassArray™ Automated Process Line, Press Release: Sep. 28, 1998, http://sequenom.com/pressrelease/92898.html.

Sequenom Uses DNA MassArray™to Sequence Section of Human Cancer–Related p53 Gene, Press Release: Mar. 27, 1998, http://sequenom.com/pressreleases/32798.html.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Sequenom Reports DNA MassArrays™ Technology More Sensitive Than Electrophoretic Methods in Detecting Gene Mutations, Press Release: Dec. 15, 1997, http://www.sequenom.com/pressrelease.htm.

Sequenom Reports On Use of Its DNA MassArray™ Technology to Analyze Genes Associated with Alzheimer's Disease and Arteriosclerosis, Press Release: Sep. 22, 1997, http://www.sequenom.com/pressrelease.htm.

Shaler et al., "Analysis of enzymatic DNA sequencing reactions by matrix–assisted laser desorption/ionization time–of–flight mass spectrometry", *Rapid Commun Mass Spectrom 9*(10):942–947 (1995).

Shaler et al., "Effect of Impurities on the matrix–Assisted Laser Desorption Mass Spectra of Single–Stranded Oligodeoxynucleotides", *Anal. Chem.* 68:576–579 (1996).

Siegel et al., Determination of distribution and loading values for calicheamicin derivatives conjugated to antibodies by matrix–assisted infrared–laser desorption/ionization mass spectrometry, Proceedings of the 42nd ASMS Conference on Mass Spectrometry, p. 967, May 29–Jun. 3, 1994.

Siegert et al., Matrix–assisted laser desorption/ionization time–of–flight mass spectrometry for the detection of polymerase hain reaction products containing 7–deasapurine moieties, *Anal. Biochem.* 243:55–65 (1996).

Singh et al., Oligonucleotides, part 5+: synthesis and fluorescence studies of DNA oligomers $d(AT)_5$ containing adenines covalently linked at C–8 with dansyl fluorophore, *Nucleic Acids Res. 18*(11):3339–3345 (1990).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Sinha et al., Polymer support oligonucleotide synthesis XVIII: Use of B–cyanoethyl–N, N–dialkylamino–/N–morpholino phosphoramidite of deoxynucleosides for the synthesis of DNA fragments simplifying deprotection and isolation of final product, *Nucleic Acids Res.* 12:4539 (1984).

Siuzdak, The emergence of mass spectrometry in biochemical research, *Proc. Natl. Acad. Sci. USA* 91:11290–11297 (1994).

Slim et al., Configurationally defined phosphorothioate–containing oligoribonucleotides in the study of the mechanism of cleavage of hammerhead ribozymes, *Nucleic Acids Res.* 19:1183–1188 (1991).

Smith R. D., New Developments in Biochemical Mass Spectrometry: Electrospray Ionization, *Anal. Chem.* 62:882–899 (1990).

Smith et al., Capillary zone electrophoresis–mass spectrometry using an electrospray ionization interface, *Anal. Chem.* 60:436–441 (1988).

Smith, Cassandra L., cDNA Fingerprinting of Breast Cancer Tumor Cells, Boston Univ., MA (1996).

Smith et al., Fluorescence detection in automated DNA sequence analysis, *Nature* 321:674–679 (1986).

Sproat et al., The synthesis of protected 5'-mercapto–2', 5'–dideoxyribonucleoside–3'–O–phosphoramidites; uses of 5'mercapto–oligodeoxyribonucleotides, *Nucleic Acids Res.* 15:4837–4848 (1987).

Sproat et al., The synthesis of protected 5'–amino–2', 5'–dideoxyribonucleoside–3'–O–phosphoramidites; applications of 5'amino–oligodeoxynucleotides, *Nucleic Acids Res.* 15:6181–6196 (1987).

Stahl, et al., "Solid phase DNA sequencing using the biotin–avidin system", *Nucleic Acids Res.* 16(7):3025–3039 (1988).

Strezoska, et al., "DNA sequencing by hybridization: 100 bases read by a non–gel–based method", *Proc. Natl. Acad. Sci. USA* 88:10089–10093 (1991).

Strupat et al., Infrared–matrix–assisted laser desorption/ionization mass spectrometry (IR–MALDI–MS) of proteins electroblotted onto polymer membranes after SDS–PAGE separation, *Mass Spectrometry in the Biological Sciences* Burlingame and Carr, eds. Humana Press, pp. 203–216 (1995).

Strupat et al., Matrix–assisted laser desorption ionization mass spectrometry of proteins electroblotted after polyacrylamide gel electrophoresis, *Anal. Chem.* 66:464–470 (1994).

Stults and Marsters, *Rapid Comm. Mass Spectrom.* 5:359–363 (1991).

Sunner et al., Graphite surface–assisted laser desorption/ionization time–of–flight mass spectrometry of peptides and proteins from liquid solutions, *Anal. Chem.* 67:4335–4342 (1995).

Sutton et al., The analysis of myocardial proteins by infrared and ultravilet laser desorption mass spectrometry, *Electrophoresis* 18:424–431 (1997).

Swerdlow and Gesteland, Capillary gel electrophoresis for rapid, high resolution DNA sequencing, *Nucleic Acids Res.* 18(6):1415–1419 (1990).

Tabor and Richardson, DNA sequence analysis with a modified bacteriophage T7 DNA polymerase, *Proc. Natl. Acad. Sci.* 84:4767–4771 (1987).

Tang et al., "Matrix–assisted laser desorption/ionization mass spectrometry of immobilized duplex DNA probes", *Nucleic Acids Research* 23:3126–3131 (1995).

Tang et al., Matrix–assisted laser desorption/ionization of restriction enzyme–digested DNA, *Rapid Commun. Mass Spectrom.* 8:183–186 (1994).

Tang, et al., Improving mass resolution in MALDI/TOF analysis of DNA.

Tang et al., Detection of 500–nucleotide DNA by laser desorption mass spectrometry, *Rapid Commun. Mass Spectrom.* 8:727–730 (1994).

Thuong and Asseline, Oligonucleotides attached to intercalators, photoreactive and cleavage agents, *Oligonucleotides and Analogues: A Practical Approach*, Eckstein, edr., Oxford University Press Ch. 12, pp. 283–308 (1991).

Tomer et al., "Coaxial Continuous Flow Fast Atom Bombardment for Higher–Molecular–Weight Peptides: Comparison with Static Fast Atom Bombardment and electrospray Ionization", *Bio Mass Spect* 20:783–788 (1991).

Tong et al., Solid–phase method for the purification of DNA sequencing reactions, *Anal. Chem.* 64:2672–2677, (1992).

Trainor, "DNA Sequencing, Automation, and the Human Genome", *Anal. Chem.* 62:418–426 (1990).

Tsarbopoulous et al., Comparative mapping of recombinant proteins and glycoproteins by plasma desorption and matrix– assisted laser desorption/ionization mass spectrometry, *Anal. Chem.* 66:2062–2070 (1994).

Valaskovic et al., "Attomole protein characterization by capillary electrophoresis–mass spectrometry", *Science* 273:1199–1202 (1996).

Valaskovic, et al., Attomole–sensitivity electrospray source for large–molecule mass spectrometry, *Anal. Chem.* 67:3802–3805 (1995).

Vorm et al., Improved resolution and very high sensivity in MALDI TOF of matrix surfaces made by fast evaporation, *Anal. Chem.* 66:3281–3287 (1994).

Wain–Hobson et al., Nucleotide sequence of the AIDS virus, LAV, *Cell* 40:9–17 (1985).

Walker et al., Multiplex strand displacement amplification (SDA) and detection of DNA sequences from *Mycobacterium tuberculosis* and other mycobacteria, *Nucleic Acids Res.* 22(13):2670–2677 (1994).

Wallace, "Ink–jet based fluid microdispensing in biochemical applications", Microfab Technologies, Inc., Laboratory Automation News, 1(5):6–9 (1996).

Wang, Solid phase synthesis of protected peptides via photolytic cleavage of the α–methylphenacyl ester anchoring linkage, *J. Org. Chem.* 41(20):3258–3261 (1976).

Wellhöner et al., Uptake and concentration of bioactive macromolecules by K562 cells via the transferrin cycle utilizing an acid–labile transferrin conjugate, *J. Biol. Chem.* 256:4309–4314, (1991).

Wiedmann M. et al., Ligase chain reaction (LCR)—overview and applications, *PCR Methods Appl.* 3(4):S51–S64 (1994).

Williams, Time of flight mass spectrometry of DNA laser–ablated from frozen aqueous solutions: applications to the Human Genome Project, *Intl. J. Mass Spectrom. and Ion Processes* 131:335–344 (1994).

Wolter et al., Negative ion FAB mass spectrometric analysis of non–charged key intermediated in oligonucleotide synthesis: rapid identification of partially protected dinucleoside monophosphates, *Biomedical Environmental Mass Spectrometry* 14:111–116 (1987).

Wong, Ch. 12: Conjugation of proteins to solid matrices, *Chemistry of Protein Conjugation and Cross Linking* 12:295–317 (1993).

Wu et al., Matrix–assisted Laser Desorption Time–of–flight Mass Spectrometry of Oligonucleotides Using 3–Hydroxypicolinic Acid as an Ultraviolet–sensitive Matrix, *Rapid Comm Mass Spec* 7:142–146 (1993).

Wu et al., Time–of–Flight Mass Spectrometry of Underivatized Single–Stranded DNA Oligomers by Matrix–Assisted Laser Desorption, *Anal. Chem.* 66:1637–1645 (1994).

Yamashita et al., Electrospray ion source. Another variation on the free–jet theme, *J. Phys. Chem.* 88:4451–4459, (1984).

Yang, et al., "Detection of hepatitis B virus in plasma using flow cytometric analyses of polymerase chain reaction–amplified DNA incorporating digoxigenin–11–dUTP", *Blood* 81(4):1083–1088 (1993).

Yates, III, Mass spectrometry and the age of the proteome, *J. Mass Spec.* 33:1–19 (1998).

Yen et al., Synthesis of water–soluble copolymers containing photocleavable bonds, *Makromol. Chem.* 190:69–82 (1989).

Zhang et al., Exploring infrared wavelength matrix–assisted laser desorption/ionization of proteins with delayed–extraction time–of–flight mass spectrometry, *J. Am. Soc. Mass Spectrom.* 9:879–884 (1998).

Zhang et al., "Single–base mutational analysis of cancer and genetic diseases using membrane bound modified oligonucleotides", *Nucl. Acids Res.* 19:3929–3933 (1991).

Zimmermann et al., Automated preparation and purification of M13 templates for DNA sequencing, *Meth. Mol. Cell. Biol.* 1:29–34 (1989).

Zuckermann et al., Efficient methods for attachment of thiol specific probes to the 3'–ends of synthetic oligodeoxyribonucleotides, *Nucleic Acids Research*, 15:13, 5305–5321 (1987).

Jespersen et al., *Mass Spectrom. in Biol Sci*, Burlingame, ed. p. 217 (1996).

Ross et al., Analysis of short tandem repeat polymorphisms in human DNA by matrix assisted laser desorption/ionization mass spectrometry, *Anal. Chem.* 69:3966–3972 (1997).

Sadeghi, *Rapid Comm. Mass Spectrom.* 11:393 (1997).

Spengler et al., *J. Phys. Chem.* 96:9678 (1992).

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:1:

CGCCTGAGTA GTACGTTCGC                                  20

(2) INFORMATION FOR SEQ ID NO:2:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:2:

GCGGTGTGTA CAAGACCCGA                                                   20
```

IR MALDI MASS SPECTROMETRY OF NUCLEIC ACIDS USING LIQUID MATRICES

BACKGROUND OF THE INVENTION

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For molecules of low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented, forming secondary ions by the so-called collision induced dissociation (CID). The fragmentation pattern/pathway very often allows the derivation of detailed structural information.

During the last decade, mass spectrometry (MS) has become an important analytical tool in the analysis of biological macromolecules. This is due at least in part to introduction of the so-called "soft ionization" methods, namely Matrix-Assisted Laser Desorption/Ionization (MALDI) and ElectroSpray Ionization (ESI), which allow intact ionization, detection and exact mass determination of large molecules, i.e. well exceeding 300 kDa in mass (Fenn, J. B., et al., (1989) *Science* 246, 64–71; Karas M. & Hillenkamp F. (1988) *Anal. Chem.* 60, 2299–3001).

MALDI-MS (reviewed in (Nordhoff E., et al., (1997) *Mass Spectrom. Rev.* 15: 67–138) and ESI-MS have been used to analyze nucleic acids. However, since nucleic acids are very polar biomolecules, that are difficult to volatize, there has been an upper mass limit for clear and accurate resolution.

ESI would seem to be superior to MALDI for the intact desorption of large nucleic acids even in the MDa mass range (Fuerstenau S. D. & Benner W. H. (1995). *Rapid Commun. Mass Spectrom.* 9, 1528–38; Chen R., Cheng X., Mitchell et al., (1995). *Anal. Chem.* 67, 1159–1163). However, mass assignment is very poor and only possible with an uncertainty of around 10%. The largest nucleic acids that have been accurately mass determined by ESI-MS, so far, are a 114 base pair double stranded PCR product (Muddiman D. C., Wunschel D. S., Lis C., Pasâ-Tolic L., Fox K. F., Fox A., Anderson G. A. & Smith R. D. (1996) *Anal. Chem.* 68, 3705–3712) of about 65 kDa in mass and a 120 nucleotide *E. coli* 5S rRNA of about 39 kDa in mass (Limbach, P. A. Crain, P. F., McCloskey, J. A., (1995) *J. Am. Soc. Mass Spectrom.* 6:27–39). ESI furthermore requires extensive sample purification.

A few reports on the MALDI-MS of large DNA molecules with lasers emitting in the ultraviolet (UV) have been reported (Ross P. L. & P. Belgrader (1997) *Anal. Chem.* 69: 3966–3972; Tang K., et al., (1994) *Rapid Commun. Mass Spectrum.* 8: 727–730; Bai J., et al., (1995) *Rapid Commun. Mass Spectrum.* 9: 1172–1176; Liu Y-H-, et al., (1995) *Anal. Chem.* 67: 3482–3490 and Siegert C. W., et al., (1997) *Anal. Biochem.* 243, 55–65. However, based on these reports it is clear that analysis of nucleic acids exceeding 30 kDa in mass (i.e. ca. a 100 mer) by UV-MALDI-MS gets increasingly difficult with a current upper mass limit of about 90 kDa (Ross P. L. & P. Belgrader (1997) *Anal. Chem.* 69: 3966–3972). The inferior quality of the DNA UV-MALDI-spectra has been attributed to a combination of ion fragmentation and multiple salt formation of the phosphate backbone. Since RNA is considerably more stable than DNA under UV-MALDI conditions, the accessible mass range for RNA is up to about 150 kDa (Kirpekar F., et al., (1994). *Nucleic Acids Res.* 22, 3866–3870).

The analysis of nucleic acids by IR-MALDI with solid matrices (mostly succinic acid and, to a lesser extent, urea and nicotinic acid) has been described (Nordhoff, E. et al., (1992) *Rapid Commun. Mass Spectrom.* 6: 771–776; Nordhoff, E. et al., (1993) *Nucleic Acids Res.* 21: 3347–3357; and Nordhoff, E. et al., (1995) *J. Mass Spec.* 30: 99–112). The 1992 Nordhoff et al., paper reports that a 20-mer of DNA and an 80-mer of RNA were about the uppermost limit for resolution. The 1993 Nordhoff et al. paper, however, provides a distinct spectra for a 26-mer of DNA and a 104-mer of tRNA. The 1995 Nordhoff et al., paper shows a substantially better spectra for the analysis of a 40-mer by UV-MALDI with the solid matrix, 3-hydroxy picolinic acid, than by IR-MALDI with succinic acid (See FIGS. 1(*d*) and 1(*e*)). In fact the 1995 paper reports that IR-MALDI resulted in a substantial degree of prompt fragmentation.

Nucleic acid analysis can be useful, for example, for diagnosing the existence of a genetic disease or chromosomal abnormality; a predisposition to a disease or condition, infection by a pathogenic organism or to provide information relating to identity, heredity or compatibility. Since mass spectrometry can be performed relatively quickly and is amenable to automation, improved methods for obtaining accurate mass spectra for larger nucleic acid molecules (e.g. larger than about 90 kDa of DNA and 150 kDa of RNA) are clearly needed.

SUMMARY OF THE INVENTION

In one aspect, the invention features processes for rapidly and accurately determining the mass of nucleic acids (e.g. DNA or RNA) using infrared matrix assisted laser desorption ionization (IR-MALDI) mass spectrometry and a liquid matrix.

In a preferred embodiment, a solution containing the nucleic acid and a liquid matrix is deposited onto a substrate to form a homogeneous, transparent thin layer of nucleic acid solution, which is then illuminated with infrared radiation, so that the nucleic acid is desorbed and ionized, thereby emitting ion particles, which are then analyzed using a mass analyzer to determine the identity of the nucleic acid. Preferably, sample preparation and deposition is performed using an automated device.

Preferred liquid matrices for use herein have a sufficient absorption at the wavelength of the laser to be used in performing desorption and ionization and are a liquid (not a solid or a gas) at room temperature (20° C.). For absorption purposes, the liquid matrix can contain at least one chromophore or functional group that strongly absorbs infrared radiation. Preferred functional groups include: nitro, sulfonyl, sulfonic acid, sulfonamide, nitrile or cyanide, carbonyl, aldehyde, carboxylic acid, amide, ester, anhydride, ketone, amine, hydroxyl, aromatic rings, dienes and other conjugated systems.

Particularly preferred liquid matrices are substituted or unsubstituted: (1) alcohols, including: glycerol, 1,2- or 1,3-propane diol, 1,2-, 1,3- or 1,4-butane diol, triethanolamine; (2) carboxylic acids including: formic acid, lactic acid, acetic acid, propionic acid, butanoic acid, pentanoic acid, hexanoic acid and esters thereof; (3) primary or secondary amides including acetamide, propanamide, butanamide, pentanamide and hexanamide, whether branched or unbranched; (4) primary or secondary amines, including propylamine, butylamine, pentylamine, hexylamine, heptylamine, diethylamine and dipropylamine; (5) nitriles, hydrazine and hydrazide.

Preferably, a liquid matrix for use herein, is miscible with a nucleic acid compatible solvent. It is also preferable that the liquid matrix is vacuum stable, i.e. has a low vapor pressure, so that the sample does not evaporate quickly in the mass analyzer. Preferably the liquid should also be of an appropriate viscosity to facilitate dispensing of micro- to nano-liter volumes of matrix alone or mixed with a nucleic acid compatible solvent. Mixtures of different liquid matrices and additives to such matrices may be desirable to confer one or more of the above-described properties.

Once prepared, the nucleic acid/matrix solution is deposited as a thin layer on a substrate, which is preferably contained within a vacuum chamber. Preferred substrates for holding the nucleic acid/matrix solution are selected from the group consisting of: beads, capillaries, flat supports, pins and wafers, with or without filter plates. Preferably the temperature of the substrate can be regulated to cool the nucleic acid/matrix solution to a temperature that is below room temperature.

Preferred infrared radiation is in the mid-IR wavelength region from about 2.5 $\mu$m to about 12 $\mu$m. Particularly preferred sources of radiation include CO, $CO_2$ and Er lasers. In certain embodiments, the laser can be an optic fiber or the laser radiation can be coupled to the mass spectrometer by fiber optics.

In a further preferred embodiment, the ion particles generated from the analyte are extracted for analysis by the mass analyzer in a delayed fashion prior to separation and detection in a mass analyzer. Preferred separation formats include linear or reflector (with linear and nonlinear fields, e.g. curved field reflectron) time-of-flight (TOF), single or multiple quadrupole, single or multiple magnetic sector, Fourier transform ion cyclotron resonance (FTICR) or ion trap mass spectrometers.

Using the processes reported herein, accurate (i.e. at least about 1% accurate) masses of sample DNA can be obtained for at least about 2000-mers of DNA (i.e. masses of at least about 650 kDa) and at least about 1200-mers of RNA (i.e. masses of at least about 400 kDa). In addition, signals of single stranded as well as double stranded nucleic acids can be obtained in the spectra.

The improved accuracy for measuring the mass of deoxyribonucleic acids (DNA) by IR-MALDI mass spectrometry (accuracy of at least about 1%) is far superior to that provided by standard agarose gel sizing of nucleic acids (accuracy of about 5%). Mass determination of ribonucleic acids (RNA) by IR-MALDI mass spectrometry (accuracy of at least about 0.5%) is even more significant, since an accurate size determination of RNA by gel analysis is difficult if not impossible, in part because of the absence of suitable size markers and of a really well-suited gel matrix.

As important as the extension in mass range is the dramatic decrease in the amount of analyte needed for preparation, down to the low femtomole (fmol) and even the attomole (amol) range even with an essentially simple preparation method. In addition, by using a liquid rather than a solid matrix, the ion signals generated have been found to be more reproducible from shot to shot. Use of a liquid matrix also facilitates sample dispensation, for example to various fields of a chip array. Further, by using a liquid matrix in conjunction with IR-MALDI mass spectrometry, essentially all sample left on the target after IR-MALDI analysis can be retrieved for further use.

Other features and advantages of the invention will be apparent from the following detailed description and claims.

BRIEF DESCRIPTION OF THE FIGURES

FIG. 1(*a*) ultraviolet matrix assisted laser desorption ionization (UV-MALDI) and detection by a linear time-of-flight (TOF) instrument using delayed extraction and a 3 hydroxypicolinic acid (3HPA) matrix (sum of 20 single shot mass spectra); FIG. 1(*b*) UV-MALDI-reflectron (ret) TOF spectrum, using delayed extraction and a 3HPA matrix (sum of 25 single shot mass spectra); and FIG. 1(*c*) IR-MALDI-retTOF spectrum, using delayed extraction and a glycerol matrix, (sum of 15 single shot mass spectra).

FIG. 2(*a*) a synthetic DNA 21 mer (sum of 10 single shot spectra); FIG. 2(*b*) a DNA mixture comprising a restriction enzyme products of a 280 mer (87 kDa), a 360 mer (112 kDa), a 920 mer (285 kDa) and a 1400 mer (433 kDa) (sum of 10 single shot spectra); FIG. 2(*c*) DNA mixture; restriction enzyme products of a 130 mer (ca. 40 kDa), a 640 mer (198 kDa) and a 2180 mer (674 kDa) (sum of 20 single shot spectra); and (d) an RNA 1206 mer (ca.387 kDa), (sum of 15 single shot spectra). Ordinate scaling is intercomparable.

DETAILED DESCRIPTION OF THE INVENTION

Figure 1A:
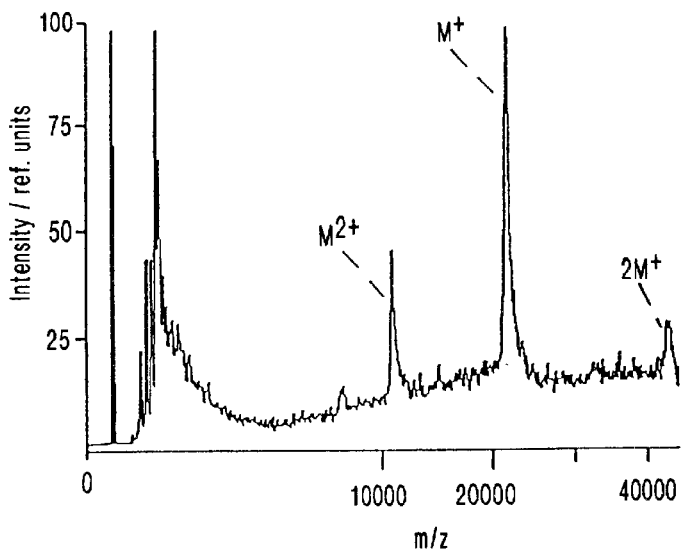
FIG. 1 shows the following mass spectra of a synthetic DNA 70-mer.

The instant invention is based, at least in part, on the surprising finding that high resolution mass spectra of large nucleic acid molecules (DNA and RNA) can be obtained by desorbing and ionizing the nucleic acids in a liquid matrix using a laser that emits in the infrared electromagnetic wavelength.

The invention therefore features a process for performing matrix assisted laser desorption ionization (MALDI) mass spectrometry, comprising mixing a nucleic acid solution with a liquid matrix to form a matrix/nucleic acid solution and depositing the solution onto a substrate to form a homogeneous, thin layer of matrix/nucleic acid solution. The nucleic acid containing substrate can then be illuminated with infrared radiation of an appropriate wavelength to be absorbed by the matrix, so that the nucleic acid is desorbed and ionized, thereby emitting ion particles that can be extracted (separated) and analyzed by a mass analyzer to determine the mass of the nucleic acid.

Nucleic acids to be analyzed according to the processes of the invention can include any single stranded or double stranded polynucleotide, such as deoxyribonucleic acid (DNA), including genomic or cDNA, ribonucleic acid (RNA) or an analog of RNA or DNA, as well as nucleotides or nucleosides and any derivative thereof. Nucleic acids can be of any size ranging from single nucleotides or nucleosides to tens of thousands of base pairs (-mers). For analysis herein, preferred nucleic acids are thousand-mers or less.

Nucleic acids may be obtained from a "biological sample" (i.e. any material obtained from any living source (e.g.

human, animal, plant, bacteria, fungi, protist, virus) using any of a number of procedures, which are well-known in the art. The particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acids from blood (Rolff, A et al., PCR: Clinical Diagnostics and Research, Springer (1994)).

Prior to being mixed with a liquid matrix, the particular nucleic acid may require further processing to yield a relatively pure nucleic acid sample. For example, a standard ethanol precipitation may be performed on restriction enzyme digested DNA. Alternatively, PCR products may require primer removal prior to analysis. Likewise, RNA strands can be separated from the molar excess of premature termination products always present in in vitro transcription reactions.

As used herein, the term "liquid matrix" is meant to refer to a matrix that has a sufficient absorption at the wavelength of the laser to be used in performing desorption and ionization and that is a liquid (not a solid or a gas) at room temperature (about 20° C.).

For absorption purposes, the liquid matrix can contain at least one chromophore or functional group that strongly absorbs infrared radiation. Examples of appropriate functional groups include: nitro, sulfonyl, sulfonic acid, sulfonamide, nitrile or cyanide, carbonyl, aldehyde, carboxylic acid, amide, ester, anhydride, ketone, amine, hydroxyl, aromatic rings, dienes and other conjugated systems.

Preferred liquid matrices are substituted or unsubstituted: (1) alcohols, including: glycerol, 1,2- or 1,3-propane diol, 1,2-, 1,3- or 1,4-butane diol, triethanolamine; (2) carboxylic acids including: formic acid, lactic acid, acetic acid, propionic acid, butanoic acid, pentanoic acid, hexanoic acid and esters thereof; (3) primary or secondary amides including acetamide, propanamide, butanamide, pentanamide and hexanamide, whether branched or unbranched; (4) primary or secondary amines, including propylamine, butylamine, pentylamine, hexylamine, heptylamine, diethylamine and dipropylamine; (5) nitriles, hydrazine and hydrazide. Particularly preferred compounds are comprised of eight or fewer carbon atoms. For example, particularly preferred carboxylic acids and amides are comprised of six or fewer carbon atoms, preferred amines are comprised of about three to about seven carbons and preferred nitriles are comprised of eight or fewer carbons. However, compounds that are unsaturated to any degree may be comprised of a larger number of carbons, since unsaturation confers liquid properties on a compound. Although the particular compound used as a liquid matrix must contain a functional group, the matrix is preferably not so reactive that it may fragment or otherwise damage the nucleic acid to be analyzed.

An appropriate liquid should also be miscible with a nucleic acid compatible solvent. Preferably the liquid should also be of an appropriate viscosity, e.g. typically less than or equal to about 1.5 $Ns/m^2$, (the viscosity of glycerol at room temperature) to facilitate dispensing of micro- to nano-liter volumes of matrix alone or mixed with a nucleic acid compatible solvent.

For use herein, a liquid matrix should also have an appropriate survival time in the vacuum of the analyzer (typically having a pressure in the range of about $10^{-5}$ to about $10^{-10}$ mbars) to allow the analysis to be completed. Liquids having an appropriate survival time are "vacuum stable", a property, which is strictly a function of the vapor pressure of the matrix, which in turn is strongly dependent on the sample temperature. Preferred matrices have a low vapor pressure at room temperature, so that less than about fifty percent of the sample in a mass analyzer having a back pressure, which is less than or equal to $10^{-5}$ mbars, evaporates in the time needed for the analysis of all samples introduced (e.g. from about 10 min to about 2 hrs.). For example, for a single sample, the analysis may be performed in minutes. However, for multiple samples, the analysis may require hours for completion.

For example, glycerol can be used as a matrix at room temperature in a vacuum for about 10 to 15 minutes. However, if glycerol is to be used for analyzing multiple samples in a single vacuum, the vacuum may need to be cooled to maintain the sample at a temperature, which is in the range of about −50° C. to about −100° C. (173 K to about 223K) for the time required to complete the analysis. Triethanolamine, in contrast, has a much lower vapor pressure than glycerol and can survive in a vacuum for at least about one hour even at room temperature.

Mixtures of different liquid matrices and additives to such matrices may be desirable to confer one or more of the above-described properties. For example, an appropriate liquid matrix could be comprised of a small amount of an IR chromophore containing solution and a greater amount of an IR invisible (i.e. nonabsorbing) material, in which, for example, the nucleic acid is soluble. It may also be useful to use a matrix, which is "doped" with a small amount of a compound or compounds having a high extinction coefficient (E) at the laser wavelength used for desorption and ionization, e.g. dinitrobenzenes, polyenes, etc. An additive that acidifies the liquid matrix may also be added to dissociate double stranded nucleic acids or to denature secondary structures of nucleic acids, such as that of t-RNA. Additional additives may be useful for minimizing salt formation between the matrix and the phosphate backbone of the nucleic acid. For example, the additive can comprise an ammonium salt or ammonium-loaded ion exchange bead, which removes alkali ions from the matrix. Alternatively, the liquid matrix can be distilled prior to mixture with the nucleic acid solution, to minimize salt formation between the matrix and the phosphate backbone of the nucleic acid.

The liquid matrix can also be mixed with an appropriate volume of water or other liquid to control sample viscosity and rate of evaporation. Since literally all of the water is evaporated during mass analysis, an easily manipulated volume (e.g. 1 $\mu$t) can be used for sample preparation and transfer, but still result in a very small volume of liquid matrix. As a result, only small volumes of nucleic acid are required to yield about $10^{-16}$ moles to about $10^{-12}$ moles (about 100 attomoles to about 1 picomole) of nucleic acid in the final liquid matrix droplet.

As shown in the following examples, when glycerol is used as a matrix, the final analyte-to-glycerol molar ratio (concentration) should be in the range of about $10^{-4}$ to $10^{-9}$ depending on the mass of the nucleic acid and the total amount of nucleic acid available. For example, for the sensitivity test described in the following examples, the relatively high concentration of nucleic acid used was measured by standard UV-spectrophotometry. Practically speaking, one typically knows the approximate amount of nucleic acid generated, e.g. from a PCR or transcription reaction. The large range specified indicates that the actual amount of nucleic acid analyzed is not very critical.

Typically, a greater amount of nucleic acid results in a better spectra. However, there may be instances where the nucleic acid sample requires dilution.

Preferably, nucleic acid samples are prepared and deposited as a thin layer (e.g. a monolayer to about a 100 $\mu$m layer, preferably between about 1 $\mu$m to 10 $\mu$m) onto a substrate using an automated device, so that multiple samples can be prepared and analyzed on a single sample support plate with only one transfer into the vacuum of the analyzer and requiring only a relatively short period of time for analysis. Appropriate automated sample handling systems for use in the instant process are described, for example, in U.S. Pat. Nos. 5,705,813, 5,716,825 and 5,498,545.

Any substrate on which the nucleic acid/liquid matrix can be deposited and retained for desorption and ionization of the nucleic acid can be used in the process of the instant invention. Preferred substrates are beads (e.g. silica gel, controlled pore glass, magnetic, Sephadex/Sepharose, cellulose), capillaries, flat supports (e.g. filters, plates or membranes made of glass, metal surfaces (steel, gold, silver, aluminum, copper or silicon) or plastic (e.g. polyethylene, polypropylene, polyamide, polyvinylidenefluoride), pins (e.g. arrays of pins suitable for combinatorial synthesis or analysis of beads in pits of flat surfaces such as wafers, with or without filter plates).

The sample containing substrate can then be analyzed in a vacuum chamber of a mass analyzer to identify the nucleic acid. Preferably, the mass analyzer can maintain the temperature of a sample at a preselected value, e.g. a temperature in the range of at least about −100° C. to about 80° C., during sample preparation, disposition or analysis. For example, improved spectra may be obtained, in some instances, by cooling the sample to a temperature below room temperature (i.e. below 20° C.) during sample preparation and/or mass analysis. Further, as described above, the vacuum stability of a matrix may be increased by cooling. Alternatively, it may be useful to heat a sample to denature double stranded nucleic acids into single strands or to decrease the viscosity during sample preparation.

Desorption and ionization of the sample is then performed in the mass analyzer using infrared radiation. "Infrared radiation" or "infrared wavelength" refers to electromagnetic wavelengths, which are longer than those of red light in the visible spectrum and shorter than radar waves. Preferred infrared wavelengths for use in the instant invention are in the mid-IR wavelength region (i.e. from about 2.5 $\mu$m to about 12 $\mu$m). Preferred sources of infrared radiation are CO lasers, which emit at about 6 $\mu$m, $CO_2$ lasers, which emit at about 9.2–11 $\mu$, Er lasers with any of a variety of crystals (e.g. YAG or YILF) emitting at wavelengths around 3 $\mu$m and and optical paramagnetic oscillator lasers emitting in the range of about 2.5 $\mu$m to about 12 $\mu$m. The pulse duration and/or size of the irradiated area (spot size) can be varied to generate multiple charged ions. A preferred pulse duration is in the range of about 100 picoseconds (ps) to about 500 nanoseconds (ns). A preferred spot size is in the range of about 50 $\mu$m in diameter to about 1 mm.

IR-MALDI can be matched with an appropriate mass analyzer, including linear (lin) or reflector (ret) (with linear and nonlinear fields, e.g. curved field reflectron) time-of-flight (TOF), single or multiple quadrupole, single or multiple magnetic sector, Fourier transform ion cyclotron resonance (FTICR) or ion trap.

Preferably detection is performed using a linear or reflectron mode TOF instrument in positive or negative ion mode, so that the ions are accelerated through a total potential difference of about 3–30 kV in the split extraction source using either static or delayed ion extraction (DE). Time-of-flight (TOF) mass spectrometers separate ions according to their mass-to-charge ratio by measuring the time it takes generated ions to travel to a detector. The technology behind TOF mass spectrometers is described for example in U.S. Pat. Nos. 5,627,369, 5,625,184, 5,498,545, 5,160,840 and 5,045,694, the teachings of which are each specifically incorporated herein by reference.

Delayed extraction with delay times ranging from about 50 ns to about 5 $\mu$s may improve the mass resolution of some nucleic acids (e.g. nucleic acids in the mass range of from about 30 kDa to about 50 kDa using either a liquid or solid matrix).

The improved processes for detecting nucleic acids by mass spectrometry can be useful, for example, for diagnosing the existence of any one of the more than 3000 known genetic diseases (Human Genome Mutations, D. N. Cooper and M. Krawczak, BIOS Publishers, 1993) including hemophilias, thalassemias, Duchenne Muscular Dystrophy (DMD), Huntington's Disease (ID), Alzheimer's Disease and Cystic Fibrosis (CF) or genetic diseases to be identified. In addition, the processes can be useful for diagnosing certain birth defects, which are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Kleinfelter's Syndrome (XXY). The processes can also be used to detect certain DNA sequences that may predispose an individual to any of a number of diseases, such as diabetes, arteriosclerosis, obesity, various autoimmune diseases and cancer (e.g. colorectal, breast, ovarian, prostate, lung) or that render an individual suitable or unsuitable for a particular medical treatment.

Alternatively, the processes can be used to detect nucleic acids that are characteristic of viruses, bacteria, fungi and other infectious organisms, which are different from the sequences contained in the host cell. Finally, the processes can be used to detect characteristic nucleic acid sequences that provide information relating to identity, heredity or compatibility.

Examples of disease causing viruses that infect humans and animals and which may be detected by the disclosed processes include: Retroviridae (e.g., human immunodeficiency viruses, such as HIV-1 (also referred to as HTLV-III, LAV or HTLV-III/LAV, See Ratner, L. et al., *Nature*, Vol. 313, Pp. 227–284 (1985); Wain Hobson, S. et al., *Cell*, Vol. 40: Pp. 9–17 (1985)); HIV-2 (See Guyader et al., *Nature*, Vol. 328, Pp. 662–669 (1987); European Patent Application No. 0 269 520; Chakraborti et al., *Nature*, Vol. 328, Pp. 543–547 (1987); and European Patent Application No. 0 655 501); and other isolates, such as HIV-LP (International Publication No. WO 94/00562 entitled "*A Novel Human Immunodeficiency Virus*"; Picornaviridae (e.g., polio viruses, hepatitis A virus, (Gust, I. D., et al., *Intervirology*, Vol. 20, Pp. 1–7 (1983); entero viruses, human coxasackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g. coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parentally transmitted (i.e., Hepatitis C); Norwalk and related viruses, astroviruses).

Examples of infectious bacteria include: *Helicobacter pyloris, Borelia burgdorferi, Legionella pneumophilia,* Mycobacteria sps (e.g. *M tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus antracis, corynebacterium diphtheriae*, corynebacterium sp., *Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue*, Leptospira, and *Actinomyces isrealli.*

Examples of infectious fungi include: *Cryptococcus neoformans, Histoplasma capsulatum, Coccidioides immitis, Blastomyces dermatidis, Chlamydia trachomatis, Candida albicans*. Other infectious organisms (i.e., protists) include: *Plasmodium falciparum* and *Tocxoplasma gondii.*

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); B. Perbal, *A Practical Guide To Molecular Cloning* (1984); the treatise, *Methods In Enzymology* (Academic Press, Inc., New York).

MALDI Mass Spectrometry of Nucleic Acids Ranging From a 70-mer to a 2180-mer

Materials and Methods

Samples

Synthetic oligodeoxynucleotides were obtained from Pharmacia Biotech (Uppsala, Sweden). The 70-mer was FPLC-purified by the supplier, while the smaller ones were used without additional purification. Plasmid DNA was purified from the *E. coli* strain DH5α by use of the Qiagen midiprep kit (QIAGEN GmbH, Hilden, Germany) according to the manufactures recommendations. Restriction enzymes were obtained from New England Biolabs GmbH (Schwalbach/Taunus, Germany); restriction enzyme digests of plasmid DNA were performed according to the supplier's protocols. Samples intended for MALDI-MS analysis were adjusted to 10 mM EDTA and 2 M $NH_4$-acetate, and precipitated with 2 volumes of ethanol. The pellet was washed once with 70% ethanol and dissolved in water to an approximate concentration of 0.5 pmol/$\mu$L.

The 1206 nucleotide in vitro transcript was synthesized and ethanol precipitated according to standard procedures (Kirkepar, F. et al., (1994) *Nucleic Acids Res.* 22: 3866–3870), using the restriction enzyme ScaI digested plasmid pBluescript KS+ as template for the T3 RNA polymerase (MBI Fermentas, Vilnius, Lithuania). A 10 $\mu$L Poros 50 R2 (PerSeptive Biosystems, Framingham, Mass.) reverse phase column was prepared and equilibrated with 3% acetonitrile/10 mM triethyl ammoniumacetate (TEAA) as described elsewhere (Kussman, M. et al., (1997) *J. Mass. Spectrom.* 32: 593–6010. The RNA sample was adjusted to 0.3 M TEAA and loaded onto the column. The column was washed with 200 $\mu$L 3% acetonitrile/10 mM TEAA, and the sample was eluted with 10 $\mu$L 25% acetonitrile/10 mM TEAA. Subsequent to lyophilization, the eluate was dissolved in 5 $\mu$L water; the estimated sample concentration was 1 pmol/$\mu$L.

A crude DNA preparation from mycoplasma-infected HELA cells was made, and a PCR performed essentially as described (Hopert, A. et al., (1993) *J. Immunol. Methods* 164: 91–100) using the primers 5'-CGC CTG AGT AGT ACG TTC GC-3' (SEQ ID NO. 1) and 5'-GCG GTG TGT ACA AGA CCC GA-3' (SEQ ID NO. 2), and recombinant Taq DNA polymerase (MBI Fermentas, Vilnius, Lithuania). The PCR results in an approximate 515 bp DNA fragment originating from the 16S rRNA gene of mycoplasma (Hopert, A. et al., (1993) *J Immunol. Methods* 164: 91–100); the precise length of the PCR product cannot be predicted because the species of the mycoplasma is unknown. A reamplification by PCR was performed under identical conditions using the same primer set, and the final product was adjusted to 4 mM EDTA/ 2M $NH_4$-acetate, and precipitated as described for the restriction enzyme digests. The pellet was dissolved in 200 $\mu$L water and purified over a Microcon-100 (Amicon GmbH, Witten, Germany) microconcentrator, by three successive diafiltrations with 100 $\mu$L water as recommended by the manufacturer. The retenate was lyophilized and re-dissolved in water to a concentration of 0.6 pmol/$\mu$L as determined by UV spectrophotometry.

Sample Preparation

For IR-MALDI, glycerol was used as the matrix. The glycerol was incubated with an equal volume of a $H^+$-cation exchange bead suspension (Dowex 50W-X8. Biorad AG, Munich, Germany) in order to reduce subsequent alkali salt formation of the nucleic acid backbone phosphates. Typically 0.5–1 $\mu$L of glycerol were mixed with an equal amount of an aqueous analyte solution on the target to give a final analyte-to-glycerol molar ratio of the sample of about $10^{-4}$–$10^{-7}$, depending, on the mass of the analyte. The mixture was smeared out evenly over an area of ca. 1–2 $mm^2$ to form a homogeneous, transparent thin layer on the stainless steel substrate. The water was evaporated off at a pressure of typically $10^{-2}$–1 Pa, before sample introduction into the mass spectrometer.

Samples for V-MALDI-MS were prepared by on-target mixing of 1 $\mu$L of a $10^{-5}$ to $10^{-6}$ M aqueous analyte solution with 0.7 $\mu$L of a 50 g/l 3-hydroxypicolinic acid (3 HPA) solution in 20% acetonitrile. About ten ammonium-loaded cation exchange beads were added to the samples before drying in a cool stream of air (Nordshoff, E. et al., (1992) *Rapid Commun. Mass Spectrom.* 60: 771–776).

Instrumental

Figure 2A:
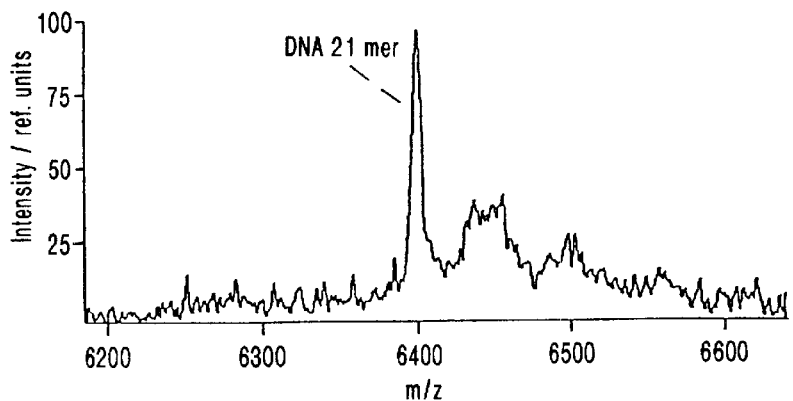
FIG. 2 shows the following IR-MALDI RetTOF mass spectra using a 2.94 $\mu$m wavelength and a glycerol matrix.

The experiments were carried out with an in-house built MALDI single stage reflectron time-of-flight (TOF) mass spectrometer of 3.5 m equivalent flight length (Berkenkamp, S. et al., (1997) *Rapid Commun. Mass Spectrom.* 11:1399–1406). The mass spectrometer can also be used in the linear TOF mode. Unless specifically mentioned, the experiments reported here have been carried out in reflectron—and positive ion mode. Ions are accelerated through a total potential difference of about 16–25 kV in the split extraction source using either static or delayed ion extraction (DE). A Venetian blind secondary electron multiplier (EMI 9643) with a conversion dynode, mounted 10 mm in front of the cathode (ion impact energy of about 20–40 kV, depending on ion mass) or a Chevron Micro-Channel plate (Galileo Co., Sturbridge, Mass., USA) are used for ion detection. For high mass ions, the potential between the conversion dynode and the electron multiplier cathode is set to several thousand volts in order to increase the ion signal by making efficient use of the secondary ions. If maximum mass resolution is sought in the mass range up to several thousand Daltons, the potential between the two electrodes is kept below about 500 V in order to detect secondary electrons only and thereby avoid the time (and mass) dispersion of the secondary ions (see e. g. FIG. 2a). Signals are processed by a transient recorder with a time resolution of about 0.5 ns (LeCroy 9350). The digitized data are transferred to a PC for storage and further evaluation. For IR-MALDI experiments, an Er-YAG -Laser emitting at 2.94 $\mu$m (Spectrum GmbH, Berlin, Germany; $\tau$=80–90 ns, energy stability ca. ±2–4% from shot to shot) was used. A frequency tripled Nd-YAG laser, emitting in the UV at 355 nm ($\tau z$=6 ns) was used for direct comparison between IR- and UV-MALDI. Single laser pulses are focused to a spot diameter of ca. 150 $\mu$m (IR) and 100 $\mu$m (UV) on the sample under an angle of 45°. Samples are observed in situ with a CCD camera of about 5 $\mu$m resolution.

Results

Figure 1B:
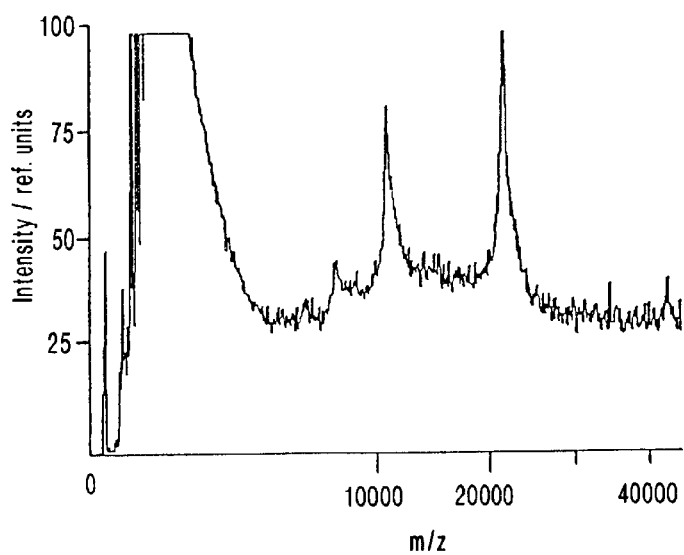
Figure 1C:
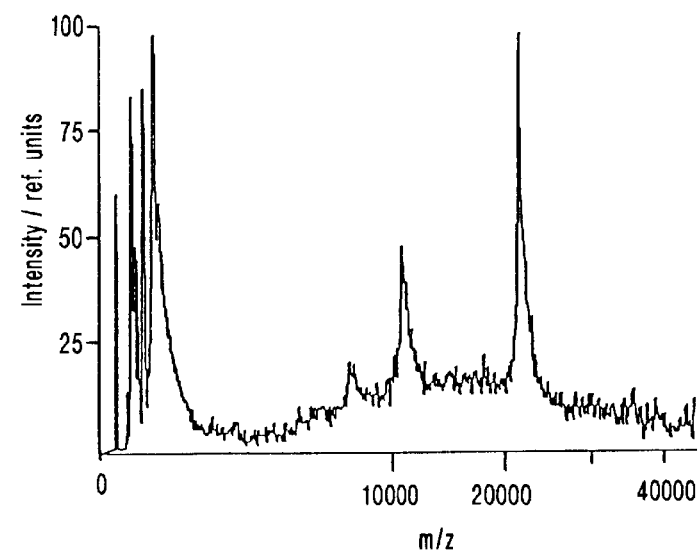

UV-MALDI spectra of DNA with at least about 50 nucleotides and with a reasonable quality could be obtained only in the linTOF, delayed-ion-extraction (DE) mode. FIGS. 1a and 1b demonstrate the striking differences in spectra quality for the two modes of operation for a synthetic DNA 70-mer (ca. 21.5 kDa) and a 3 HPA matrix (355 nm). The quality of the spectrum of FIG. 1b, obtained in reflectron mode is quite inferior to that of FIG. 1a in several respects. Signal intensity as well as signal-to-noise ratio are considerably degraded as is the mass resolution, down to 15 (M/$\Delta$m; FWHM) from 65 in the spectrum of FIG. 1a. The saturated signal in the mass range below approximately 2000 Da in FIG. 2b reflects the increased laser fluence necessary to obtain analyte signals of the intensity shown. The loss in mass resolution is, for the most part, a result of the sloping low mass edge of the peaks, signaling abundant metastable small neutral losses. Exact mass determination is severely compromised by the loss of spectral quality. The IR-MALDI spectrum (refTOF, DE mode) of the same DNA 70-mer with glycerol as matrix is shown in FIG. 1c. The quality of this spectrum is comparable to UV-MALDI analysis obtained in the linear mode with respect to signal intensity and mass resolution (FIG. 1a). The base peak has a steeply rising low mass edge, demonstrating an essential absence of any metastable small neutral loss. This behavior was consistently observed for IR-MALDI of nucleic acid with glycerol as a matrix, qualifying it as a very gentle desorption method forming ions of nucleic acids of high ion stability. This contrasts strikingly to the IR-MALDI spectra of nucleic acids obtained with succinic acid as matrix (Nordhoff, E. et al., (1993) *Nucl. Acids Res.* 21: 3347–3357; FIGS. 1(d) and 1(c)). The absence of literally all metastable neutral loss for the glycerol matrix, therefore, was a very unexpected result not anticipated based on prior experience (See the Background of the Invention).

This leads to a broad mass range for the analysis of nucleic acids, from small oligonucleotides up to more than 2000 nt. as demonstrated in FIG. 2. A refTOF mass spectrum of a synthetic DNA 21-mer is shown in FIG. 2a. With delayed ion extraction a mass resolution of 1050 (FWHM) is obtained, comparable to the resolution obtained with the instrument for proteins in this mass range. Several poorly resolved peaks on the high mass side of the analyte peak appear in the spectrum. They are detection artifacts of residual secondary ions generated at the conversion dynode operated here in a mode to preferentially detect only secondary electrons in order to not degrade mass resolution by the ion detection system. FIG. 2b demonstrates the high mass range with a restriction enzyme digest of a plasmid (pBluescript-KS+ digested with Bgll and RsaI), yielding four fragments of 280 bp, 360 bp, 920 bp, and 1,400 bp. All four signals represent single strands and are the composite signal of the two complementary strands. Very weak, if any signals of the double stranded oligomers are apparent in this spectrum. Tentatively, the dissociation of the double strands in samples prepared with purified glycerol is attributed to an acidification by the H$^+$ion exchange resin. Not enough experience has, however, been accumulated so far to identify all additional parameters determining double strand dissociation under IR-MALDI conditions. The mass resolution of all high mass ion signals is about 50 (FWHM) and appears to be relatively independent of the ion mass. The IR-MALDI mass spectrum of FIG. 1c shows the upper mass limit measured so far for a restriction enzyme digest (130 bp, 640 bp, and 2,180 bp). The signal of the 2,180 nt ss-fragment was obtained only after heating the restriction digest to a temperature of 95° C. for 5 minutes. Such large DNA fragments apparently do not get separated into single strands under the conditions used, in contrast to the samples up to 1400 bp. The relatively poor mass resolution of ca. 30 for the 2,180 nt fragment in this spectrum and the strong background signals indicate an upper mass limit for IR-MALDI-MS of nucleic acids of approximately 700 kDa under the current conditions. Accordingly, the double stranded 2,180 nt fragment was not observable.

Figure 2B:
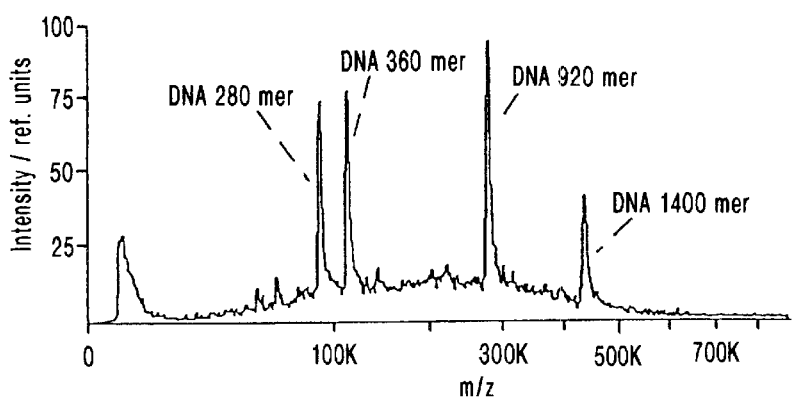
Figure 2C:
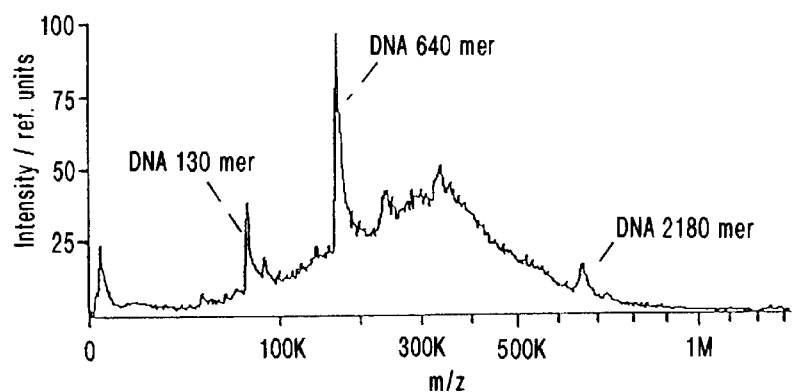
Figure 2D:
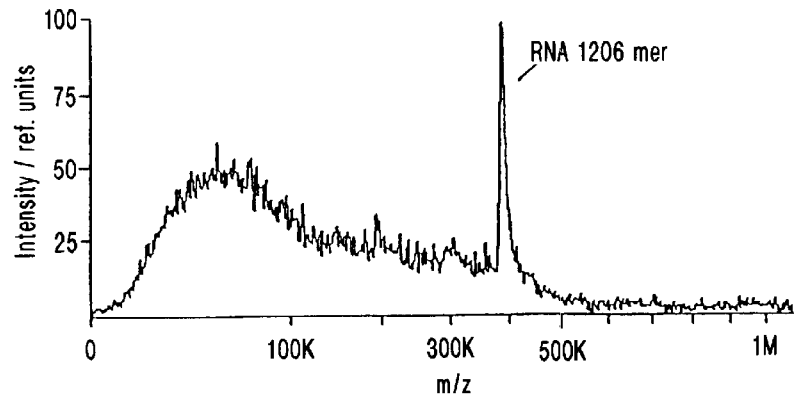

IR-MALDI-MS of- large RNA is also possible as shown in FIG. 2d for an RNA 1206 nt in vitro transcript. The increased ion-stability for RNA compared to DNA, well documented for UV-MALDI, was not observed in IR-MALDI within the mass range tested in these experiments. Large DNA ions as well as large RNA appeared to be of comparable stability, stable enough even for TOF analysis in the reflectron mode. The large hump, centered at about 50 kDa is believed to reflect impurities of the sample rather than metastable fragments. The comparably steep rise of the peak at the low mass side also testifies to a very limited loss of small neutrals such as single bases.

One advantage of glycerol as matrix is the superior shot to shot reproducibility and mass precision (200–400 ppm) (Nordhoff, E. et al., (1993) *Nucleic Acids Res.* 21: 3347–3357. These values, originally determined for proteins, are also valid for the analysis of smaller oligonucleotides. However, mass accuracy was found to be mass dependent. Using, an external 2 point calibration with angiotensin II (1047 Da) and bovine insulin (5743 Da) the mass of the 21 mer (6398 Da) in FIG. 2a was determined to within ±2 Da of the known mass, i.e. an accuracy of 0.03%. The molecular mass of the 70 mer (theoretical mass: 21517 Da) was determined to within ±25 Da i.e. a mass accuracy of 0.1% from the spectrum of FIG. 1c, calibrated with cytochrome C oligomers. ($M^+$, $2M^{30}$, $3M^+$).

For all of the ten different samples of high mass DNA analyzed, the measured mass was within less than about 1% of the theoretical mass derived from the sequence (see e g. FIGS. 2b and 2c). The average mass of the two single strands was used as the theoretical mass in the case of DNA restriction enzyme fragments. The masses of the two single strands never differed by more than about 1%. Only one large mass RNA has been measured so far (FIG. 2d). The measured mass of this RNA is 388,270 Da, whereas the mass calculated from the gene sequence is 386,606 Da. Given that the sample most likely is a heterogeneous mixture of the species expected from the gene sequence with less abundant products extended by one to three extra nucleotides (Melton, D. A. et al., (1984) *Nucleic Acids Res.* 12: 7035–7056), the actual mass of the RNA sample is probably about 500 Da larger than the one calculated from the sequence. It would therefore appear as though a mass accuracy of at least about 1% as observed for DNA, can also be achieved for RNA.

For external 4 point calibrations of large DNA/RNA with molecular masses between 100–400 kDa, either clusters of cytochrome C (e.g. $10M^+$, $20M^+$, $30M^+$, $40M^+$) or multimers of an IgG monoclonal antibody (e.g. $2M^+$$3M^+$, $4M^+$) were used. For analytes exceeding 500 kDa the calibration with IgG monoclonal antibody was found to be most exact. Mass calibration of unknown DNA fragments using DNA or RNA calibrants may be more desirable, resulting in a more accurate mass determination.

Figure 3A:
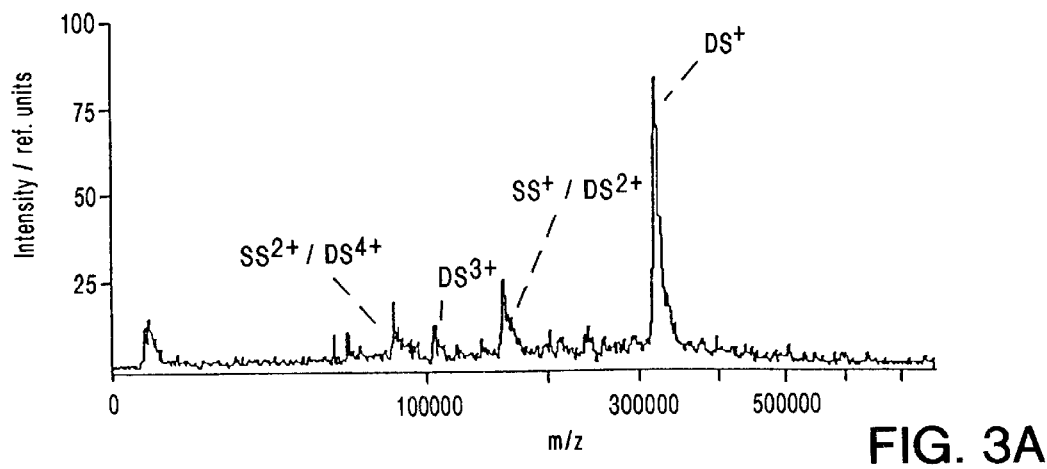
FIG. 3 shows the spectra of a 515-mer double stranded PCR DNA product. The following different total amounts of sample were loaded: 3(*a*) 300 fmol, single shot spectrum; 3(*b*) 3 fmol, sum of single shot spectra; 3(*c*) 300 amol, sum of 25 single shot spectra obtained using an IR-MALDI RetTOF, wherein the laser emitted at a wavelength of 2.94 $\mu$m using a glycerol matrix.

Experiments to evaluate the sensitivity of IR-MALDI-MS of large nucleic acids with glycerol as matrix have been carried out with a PCR-product of approximately 515 nt and unknown sequence. Its mass was measured to 318,480 Da. For these measurements, glycerol, not subjected to ion exchange purification, was used. The spectra show dominant signals of the double stranded moiety. Tentatively the dissociation of the double strands in samples prepared with purified glycerol is attributed to an acidification of the glycerol by the protons exchanged for the cations. Although additional parameters may be involved in the double strand dissociation under IR-MALDI conditions. The starting concentration for the dilution experiment was 0.6 pmol/L as determined by UV spectrophotometry. The mass spectra in FIG. 3 were obtained by loading different amounts of sample onto the target. For the single shot mass spectrum in FIG. 3a, 300 fmol of the PCR-product had been loaded. The quality of this spectrum with an S/N-ratio better than 100 and a mass resolution of 65 (FWHM) for the double-strand indicates that the analyte to matrix ratio (A/M) of about $10^{-7}$ is well suited for an analyte of this size (about 320 kDa).

Figure 3B:
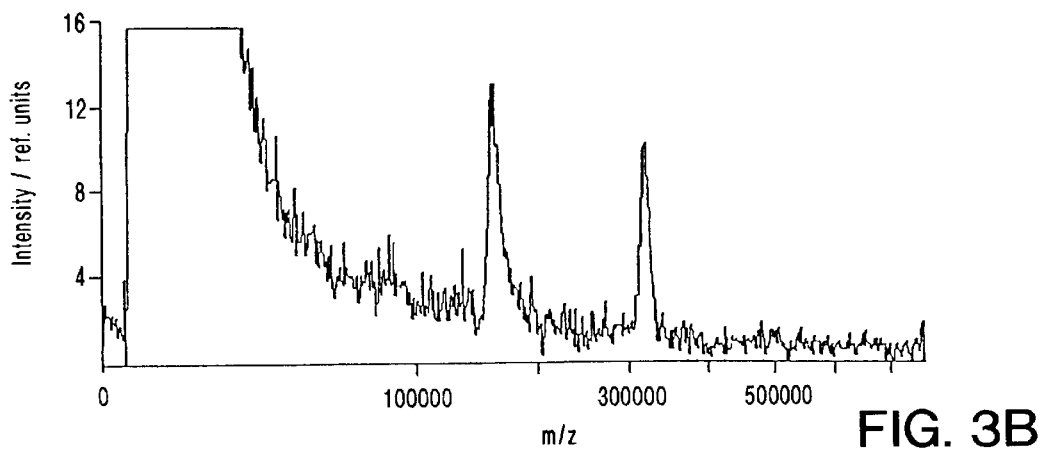
Figure 3C:
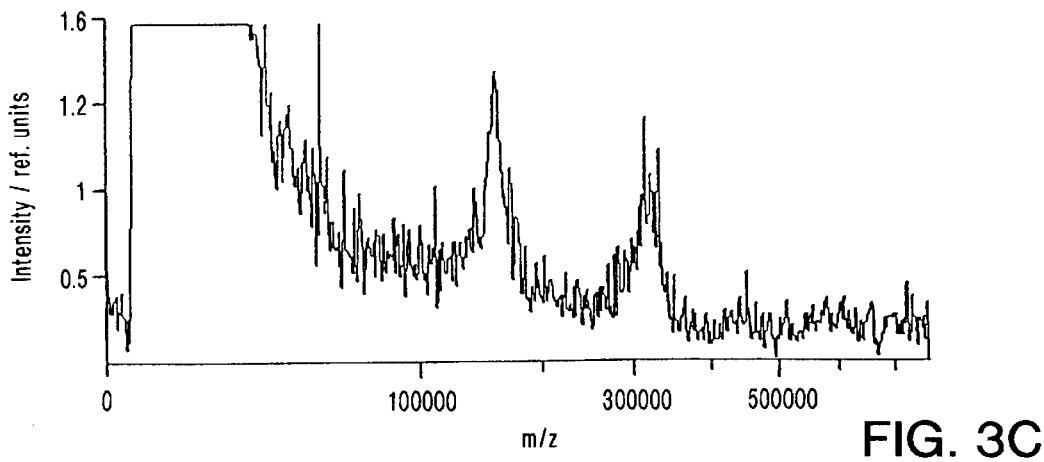

The mass spectrum in FIG. 3b was obtained using a 3 fmol total load (A/M about $2\times10^{-9}$). A strong background signal now dominates the low mass range. Total signal intensity, mass resolution (of about 25 FWHM for the ds-ion signal) and S/N-ratio are significantly degraded compared to FIG. 3a. However, mass determination is still possible with an accuracy of about 1%. The spectrum in FIG. 3c has been obtained from a very small sample volume forming an approximately 270 μm diameter sample spot on the target and a total sample load of only 300 amol (A/M about $8\times10^{-10}$). Such small sample volumes can be realized by either dispensing the small volumes by micropipettes as described in the literature (See e.g. Little, D. P., (1997) *Anal. Chem.* 69: 4540–4546) or by preparing the analyte in a standard microliter volume of a suitable glycerol/water mixture. In the latter case, the water is then evaporated off prior to or upon insertion of the sample into the vacuum. The poor mass resolution of only about 10 classifies this amount of analyte as the limit for the given instrument and detection system for a mass accuracy of better than about 3%. Compared to values reported for UV-MALDI-MS (Tang, K. et al., (1994) *Rapid Commun. Mass Spectrom.* 8: 727–730; and FIGS. 5 and 6), the sensitivity demonstrated here for IR-MALDI-MS demonstrates an improvement of at least about 2–3 orders of magnitude for nucleic acids of this size.

What is claimed is:

1. A process for performing matrix assisted laser desorption/ionization (MALDI) of a nucleic acid and analysis by mass spectrometry, comprising the steps of:
   (a) depositing a solution containing the nucleic acid and a liquid matrix on a substrate to form a homogeneous, thin layer of a nucleic acid/liquid matrix solution, wherein:
      the liquid matrix comprises glycerol, 1,2- or 1,3- propane diol, 1,2-, 1,3-or 1,4- butane diol and triethanolamine;
   (b) illuminating the substrate with infrared radiation, whereby the nucleic acid in the solution is desorbed and ionized; and
   (c) determining the mass of the nucleic acid by a mass spectrometric format for separation and detection of desorbed and ionized molecules, wherein the mass of the nucleic acid molecule is at least about 90 kD and the accuracy for determining the mass of the nucleic acid is within about 1%.

2. A process of claim 1, wherein:
   the liquid matrix is comprised of the alcohol and an additional liquid, which confers to the liquid matrix at least one of the properties selected from the group consisting of i) miscibility with a nucleic acid compatible solvent, ii) vacuum stability, and, iii) an appropriate viscosity to facilitate dispensing of micro- to nanoliter volumes of matrix alone or mixed with a nucleic acid compatible solvent.

3. A process of claim 1, wherein the liquid matrix comprises an additive.

4. A process of claim 3, wherein the additive is selected from the group consisting of a compound having a high extinction coefficient at the laser wavelength used for the analysis, an additive that acidifies the liquid matrix, and an additive that minimizes salt formation between the liquid matrix and the phosphate backbone of the nucleic acid.

5. A process of claim 1, wherein prior to step (a), the liquid matrix is treated to minimize salt formation between the matrix and the phosphate backbone of the nucleic acid.

6. A process of claim 5, wherein the liquid matrix is treated by distillation or ion exchange.

7. A process of claim 1, wherein the liquid matrix is glycerol.

8. A process of claim 7, wherein the final analyte-to-glycerol molar ratio is about $10^{-4}$ to about $10^{-9}$ depending on the mass of the nucleic acid and the total sample volume.

9. A process of claim 1, wherein the liquid matrix is glycerol, the mass of the nucleic acid is in the range of from about $10^4$ to about $10^6$ Da and the glycerol is subjected to ion exchange prior to step (a).

10. A process of claim 1, wherein the nucleic acid is DNA.

11. A process of claim 10, the DNA is less than or equal to about a 2000-mer.

12. A process of claim 1, wherein the nucleic acid is RNA.

13. A process f claim 12, wherein the RNA is less than or equal to about a 1200-mer.

14. A process of claim 1, wherein the infrared radiation is of a wavelength in the range of from about 2.5 $\mu$m to about 12 $\mu$m.

15. A process of claim 1, wherein the radiation pulses have a width in the range of about 500 ps to about 500 ns.

16. A process of claim 1, wherein the infrared radiation is generated from a source selected from the group consisting of a CO laser, a $CO_2$ laser, en Er laser and an optical parametric oscillator laser emitting in the range of about 2.5 to about 12 $\mu$m.

17. A process of claim 1, wherein the sample contains less than about 10 pmoles of nucleic acid.

18. A process of claim 1, wherein step (a) is automated.

19. A process of claim 1, wherein the sample, which with the matrix remains in a liquid or glass state, is cooled to a temperature, which is below about 20° C.

20. A process of claim 1, wherein the sample, which remains in a liquid state, is heated to a temperature which is greater than about 20° C. and less than about 80° C.

21. A process of claim 1, wherein prior to step (c), the nucleic acid ions are extracted from the ion source by delayed extraction.

22. A process of claim 1, wherein the mass spectrometric format is selected from the group consisting of time-of-flight (TOF), quadrupole, magnetic sector, Fourier transform ion cyclotron resonance (FTICR), ion trap and combinations thereof.

23. A process of claim 22, wherein a mass spectrometry format is TOF and the TOF is linear.

24. A process of claim 22, wherein a mass spectrometry format is TOF and the TOF has a reflector.

25. A process of claim 22, wherein a mass spectrometry format is TOF and the TOF reflector has a linear field.

26. A process of claim 22, wherein a mass spectrometry format is TOF reflector has a nonlinear field.

27. A process of claim 22, wherein a mass spectrometry format is quadrupole and the quadrupole is single.

28. A process of claim 22, wherein a mass spectrometry format is quadrupole and the quadrupole is multiple.

29. A process of claim 22, wherein a mass spectrometry format is magnetic sector and the magnetic sector is single.

30. A process of claim 22, wherein a mass spectrometry format is magnetic sector and the magnetic sector is multiple.

* * * * *

UNITED STATES PATENT AND TRADEMARK OFFICE
CERTIFICATE OF CORRECTION

PATENT NO.   : 6,723,564 B2
DATED        : April 20, 2004
INVENTOR(S)  : Franz Hillenkamp It is certified that error appears in the above-identified patent and that said Letters Patent is hereby corrected as shown below:

Column 16,
Lines 52-53, please replace Claim 26, with the following Claim:

26. A process of claim 22, wherein a mass spectrometry format is TOF and the TOF reflector has a nonlinear field Signed and Sealed this Twenty-fourth Day of August, 2004

JON W. DUDAS
*Director of the United States Patent and Trademark Office*